(12) United States Patent
Christianson et al.

(10) Patent No.: US 10,595,996 B2
(45) Date of Patent: *Mar. 24, 2020

(54) THROMBUS MANAGEMENT AND STRUCTURAL COMPLIANCE FEATURES FOR PROSTHETIC HEART VALVES

(71) Applicant: Tendyne Holdings, Inc., Roseville, MN (US)

(72) Inventors: Mark Christianson, Plymouth, MN (US); Chad Perrin, Andover, MN (US); Zachary Tegels, Minneapolis, MN (US); Craig Ekvall, East Bethel, MN (US); Robert Vidlund, Forest Lake, MN (US); Son Mai, Centerville, MN (US); Michael Evans, Minneapolis, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 330 days.

This patent is subject to a terminal disclaimer.

(21) Appl. No.: 15/456,022

(22) Filed: Mar. 10, 2017

(65) Prior Publication Data

US 2017/0181854 A1 Jun. 29, 2017

Related U.S. Application Data

(60) Division of application No. 14/976,866, filed on Dec. 21, 2015, now Pat. No. 9,597,181, which is a
(Continued)

(51) Int. Cl.
*A61F 2/24* (2006.01)

(52) U.S. Cl.
CPC .......... *A61F 2/2448* (2013.01); *A61F 2/2412* (2013.01); *A61F 2/2418* (2013.01);
(Continued)

(58) Field of Classification Search
None
See application file for complete search history.

(56) References Cited

U.S. PATENT DOCUMENTS

| 2,697,008 A | 12/1954 | Rowley |
| 3,409,013 A | 11/1968 | Berry |
| | (Continued) | |

FOREIGN PATENT DOCUMENTS

| CN | 1486161 | 3/2004 |
| CN | 1961845 A | 5/2007 |
| | (Continued) | |

OTHER PUBLICATIONS

US 9,155,620 B2, 10/2015, Gross et al. (withdrawn)
(Continued)

*Primary Examiner* — Megan Y Wolf
(74) *Attorney, Agent, or Firm* — Lerner, David, Littenberg, Krumholz & Mentlik, LLP

(57) ABSTRACT

A prosthetic heart valve can include an outer support assembly, an inner valve assembly, which define between them an annular space, and a pocket closure that bounds the annular space to form a pocket in which thrombus can be formed and retained. Alternatively, or additionally, the outer support assembly and the inner valve assembly can be coupled at the ventricle ends of the outer support assembly and the inner valve assembly, with the outer support assembly being relatively more compliant in hoop compression in a central, annulus portion than at the ventricle end, so that the prosthetic valve can seat securely in the annulus while imposing minimal loads on the inner valve assembly that could degrade the performance of the valve leaflets.

13 Claims, 24 Drawing Sheets

Related U.S. Application Data continuation of application No. PCT/US2014/044047, filed on Jun. 25, 2014, which is a continuation-in-part of application No. 14/155,535, filed on Jan. 15, 2014, now abandoned.

(60) Provisional application No. 61/840,313, filed on Jun. 27, 2013, provisional application No. 61/839,237, filed on Jun. 25, 2013.

(52) U.S. Cl.
CPC .......... *A61F 2/2463* (2013.01); *A61F 2/2457* (2013.01); *A61F 2/2487* (2013.01); *A61F 2210/0014* (2013.01); *A61F 2220/0025* (2013.01); *A61F 2220/0075* (2013.01); *A61F 2230/001* (2013.01); *A61F 2230/0034* (2013.01); *A61F 2230/0093* (2013.01); *A61F 2250/006* (2013.01); *A61F 2250/0018* (2013.01); *A61F 2250/0023* (2013.01); *A61F 2250/0024* (2013.01); *A61F 2250/0039* (2013.01); *A61F 2250/0069* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Sammuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |

(56) References Cited

U.S. PATENT DOCUMENTS

| | | |
|---|---|---|
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro et al. |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely et al. |
| 6,575,252 B2 | 6/2003 | Reed |
| 6,582,462 B1 | 6/2003 | Andersen et al. |
| 6,605,112 B1 | 8/2003 | Moll |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |

(56) References Cited

U.S. PATENT DOCUMENTS

| | | |
|---|---|---|
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |
| 8,052,749 B2 | 11/2011 | Salahieh |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Thambar et al. |
| 8,986,376 B2 | 3/2015 | Solem |
| 9,011,522 B2 | 4/2015 | Annest et al. |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Sequin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 * | 3/2017 | Christianson ......... A61F 2/2418 |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0032481 A1 | 3/2002 | Gabbay |
| 2002/0116054 A1 | 8/2002 | Lundell et al. |
| 2002/0138138 A1 | 9/2002 | Yang |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | Van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |

(56) References Cited

U.S. PATENT DOCUMENTS

| | | |
|---|---|---|
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0149350 A1 | 7/2006 | Patel et al. |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Randert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |

(56) References Cited

U.S. PATENT DOCUMENTS

| | | |
|---|---|---|
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022633 A1 | 1/2012 | Olson et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0158129 A1 | 6/2012 | Duffy et al. |
| 2012/0165930 A1 | 6/2012 | Gifford et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0325114 A1* | 12/2013 | McLean ............. A61F 2/2427 623/2.12 |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0249622 A1 | 9/2014 | Carmi et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund et al. |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James et al. |
| 2015/0202044 A1 | 7/2015 | Chau et al. |
| 2015/0216653 A1 | 8/2015 | Freudenthanl |
| 2015/0216660 A1 | 8/2015 | Pintor et al. |
| 2015/0223820 A1 | 8/2015 | Olson et al. |
| 2015/0223934 A1 | 8/2015 | Vidlund et al. |
| 2015/0238312 A1 | 8/2015 | Lashinski |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean et al. |
| 2015/0335424 A1 | 11/2015 | McLean et al. |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |

(56) References Cited

U.S. PATENT DOCUMENTS

| | | |
|---|---|---|
| 2016/0074160 A1 | 3/2016 | Christianson et al. |
| 2016/0106537 A1 | 4/2016 | Christianson et al. |
| 2016/0113764 A1 | 4/2016 | Sheahan et al. |
| 2016/0143736 A1 | 5/2016 | Vidlund et al. |
| 2016/0151155 A1 | 6/2016 | Lutter et al. |
| 2016/0206280 A1 | 7/2016 | Vidlund et al. |
| 2016/0242902 A1 | 8/2016 | Morriss et al. |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau et al. |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1 | 3/2017 | Vidlund et al. |
| 2017/0100248 A1 | 4/2017 | Tegels et al. |
| 2017/0128208 A1 | 5/2017 | Christianson et al. |
| 2017/0196688 A1 | 7/2017 | Christianson et al. |
| 2017/0252153 A1 | 9/2017 | Chau et al. |
| 2017/0266001 A1 | 9/2017 | Vidlund et al. |
| 2017/0281343 A1 | 10/2017 | Christianson et al. |
| 2017/0312076 A1 | 11/2017 | Lutter et al. |
| 2017/0312077 A1 | 11/2017 | Vidlund et al. |
| 2017/0319333 A1 | 11/2017 | Tegels et al. |
| 2018/0028314 A1 | 2/2018 | Ekvall et al. |
| 2018/0078368 A1 | 3/2018 | Vidlund et al. |
| 2018/0078370 A1 | 3/2018 | Kovalsky et al. |
| 2018/0147055 A1 | 5/2018 | Vidlund et al. |
| 2018/0193138 A1 | 7/2018 | Vidlund |

FOREIGN PATENT DOCUMENTS

| | | |
|---|---|---|
| CN | 2902226 | 5/2007 |
| CN | 101146484 | 3/2008 |
| CN | 101180010 | 5/2008 |
| CN | 101984938 | 3/2011 |
| CN | 102869317 | 1/2013 |
| CN | 102869318 | 1/2013 |
| CN | 102869321 | 1/2013 |
| CN | 103220993 | 7/2013 |
| CN | 102639179 B | 10/2014 |
| DE | 2246526 | 3/1973 |
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049815 | 4/2002 |
| DE | 102006052564 | 12/2007 |
| DE | 102006052710 | 5/2008 |
| DE | 102007043830 A1 | 4/2009 |
| DE | 102007043831 | 4/2009 |
| EP | 0103546 | 5/1988 |
| EP | 1057460 | 12/2000 |
| EP | 1088529 | 4/2001 |
| EP | 1469797 | 11/2005 |
| EP | 2111800 | 10/2009 |
| EP | 2193762 | 6/2010 |
| EP | 2747707 | 4/2015 |
| EP | 2918248 | 9/2015 |
| EP | 2278944 | 3/2016 |
| FR | 2788217 | 7/2000 |
| FR | 2815844 | 5/2002 |
| JP | 2003-505146 | 2/2003 |
| JP | 2005-515836 | 6/2005 |
| JP | 2009-514628 | 4/2009 |
| JP | 2009-519783 | 5/2009 |
| JP | 2013-512765 | 4/2013 |
| NL | 1017275 | 8/2002 |
| SU | 1271508 | 11/1986 |
| WO | WO 92/17118 | 10/1992 |
| WO | WO 93/01768 | 2/1993 |
| WO | WO 98/29057 | 7/1998 |
| WO | WO 99/40964 | 8/1999 |
| WO | WO 99/47075 | 9/1999 |
| WO | WO 2000/018333 | 4/2000 |
| WO | WO 2000/030550 | 6/2000 |
| WO | WO 2000/041652 | 7/2000 |
| WO | WO 2000/047139 | 8/2000 |
| WO | WO 2001/035878 | 5/2001 |
| WO | WO 2001/049213 | 7/2001 |
| WO | WO 2001/054624 | 8/2001 |
| WO | WO 2001/054625 | 8/2001 |
| WO | WO 2001/056512 | 8/2001 |
| WO | WO 2001/061289 | 8/2001 |
| WO | WO 2001/076510 | 10/2001 |
| WO | WO 2001/082840 | 11/2001 |
| WO | WO 2002/004757 | 1/2002 |
| WO | WO 2002/022054 | 3/2002 |
| WO | WO 2002/028321 | 4/2002 |
| WO | WO 2002/036048 | 5/2002 |
| WO | WO 2002/041789 | 5/2002 |
| WO | WO 2002/043620 | 6/2002 |
| WO | WO 2002/049540 | 6/2002 |
| WO | WO 2002/076348 | 10/2002 |
| WO | WO 2003/003943 | 1/2003 |
| WO | WO 2003/030776 | 4/2003 |
| WO | WO 2003/047468 | 6/2003 |
| WO | WO 2003/049619 | 6/2003 |
| WO | WO 2004/019825 | 3/2004 |
| WO | WO 2005/102181 | 11/2005 |
| WO | WO 2006/014233 | 2/2006 |
| WO | WO 2006/034008 | 3/2006 |
| WO | WO 2006/064490 | 6/2006 |
| WO | WO 2006/070372 | 7/2006 |
| WO | WO 2006/105009 | 10/2006 |
| WO | WO 2006/113906 | 10/2006 |
| WO | WO 2006/127756 | 11/2006 |
| WO | WO 2007/081412 | 7/2007 |
| WO | WO 2007/100408 | 9/2007 |
| WO | WO 2008/005405 | 1/2008 |
| WO | WO 2008/035337 | 3/2008 |
| WO | WO 2008/091515 | 7/2008 |
| WO | WO 2008/125906 | 10/2008 |
| WO | WO 2008/147964 | 12/2008 |
| WO | WO 2008/150529 | 12/2008 |
| WO | WO 2009/024859 | 2/2009 |
| WO | WO 2009/026563 | 2/2009 |
| WO | WO 2009/045338 | 4/2009 |
| WO | WO 2009/132187 | 10/2009 |
| WO | WO 2010/090878 | 8/2010 |
| WO | WO 2010/098857 | 9/2010 |
| WO | WO 2010/121076 | 10/2010 |
| WO | WO 2011/017440 | 2/2011 |
| WO | WO 2011/022658 | 2/2011 |
| WO | WO 2011/069048 | 6/2011 |
| WO | WO 2011/072084 | 6/2011 |
| WO | WO 2011/106735 | 9/2011 |
| WO | WO 2011/109813 | 9/2011 |
| WO | WO 2011/159342 | 12/2011 |
| WO | WO 2011/163275 | 12/2011 |
| WO | WO 2012/027487 | 3/2012 |
| WO | WO 2012/036742 | 3/2012 |
| WO | WO 2012/095116 | 7/2012 |
| WO | WO 2012/177942 | 12/2012 |
| WO | WO 2013/028387 | 2/2013 |
| WO | WO 2013/045262 | 4/2013 |
| WO | WO 2013/059747 | 4/2013 |
| WO | 2013072496 A1 | 5/2013 |
| WO | WO 2013/096411 | 6/2013 |
| WO | WO 2013/175468 | 11/2013 |
| WO | WO 2014/121280 | 8/2014 |
| WO | WO 2014/144937 | 9/2014 |
| WO | WO 2014/162306 | 10/2014 |
| WO | WO 2014/189974 | 11/2014 |
| WO | WO 2014/210124 | 12/2014 |
| WO | WO 2015/051430 | 4/2015 |
| WO | WO 2015/058039 | 4/2015 |
| WO | WO 2015/063580 | 5/2015 |
| WO | WO 2015/065646 | 5/2015 |

(56) References Cited

FOREIGN PATENT DOCUMENTS

| WO | WO 2015/120122 | 8/2015 |
|---|---|---|
| WO | WO 2015/138306 | 9/2015 |
| WO | WO 2015/173609 | 11/2015 |
| WO | WO 2016/112085 | 7/2016 |
| WO | WO 2016/126942 | 8/2016 |
| WO | WO 2016/168609 | 10/2016 |
| WO | WO 2016/196933 | 12/2016 |
| WO | WO 2017/096157 | 6/2017 |
| WO | WO 2017/132008 | 8/2017 |
| WO | WO 2017/218375 | 12/2017 |
| WO | WO 2018/005779 | 1/2018 |
| WO | WO 2018/013515 | 1/2018 |

OTHER PUBLICATIONS

Notice of Reasons for Rejection for Japanese Application No. 2016-521909, dated Mar. 27, 2018, 10 pages.
First Office Action for Chinese Application No. 201480035996.8, dated Dec. 5, 2016, 12 pages.
Second Office Action for Chinese Application No. 201480035996.8, dated Aug. 1, 2017, 8 pages.
Communication Pursuant to Article 94(3) EPC for European Application No. 14739333.4, dated Oct. 20, 2016, 6 pages.
International Search Report and Written Opinion for International Application No. PCT/US2014/044047, dated Nov. 17, 2014, 15 pages.
Office Action for U.S. Appl. No. 14/976,866, dated May 25, 2016, 13 pages.
Al Zaibag, M. et al., "Percutaneous Balloon Valvotomy in Tricuspid Stenosis," British Heart Journal, Jan. 1987, 57(1):51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
Andersen, H. R. et al., "Transluminal implantation of artificial heart valves. Description of a new expandable aortic valve and initial results with implantation by catheter technique in closed chest pigs," European Heart Journal, 1992, 13(5):704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Ashton, R. C., Jr. et al., "Development of an Intraluminal Device for the Treatment of Aortic Regurgitation: Prototype and in Vitro Testing System," Journal of Thoracic and Cardiovascular Surgery, 1996, 112:979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
Bernacca, G. M. et al., "Polyurethane heart valves: Fatigue failure, calcification, and polyurethane structure," Journal of Biomedical Materials Research, Mar. 5, 1997, 34(3):371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive CardioVascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L. L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-arteries-gets-a-faili . . . ,>, published Jan. 3, 1991, retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, G. et al., "Mitral Valved Stent Implantation," European Journal of Cardio-Thoracic Surgery, 2010, 38:350-355, 2 pages.
Ma, L. et al., "Double-crowned valved stents for off-pump mitral valve replacement," European Journal of Cardio-Thoracic Surgery, Aug. 2005, 28(2):194-198.
Moazami, N. et al., "Transluminal aortic valve placement: A feasibility study with a newly designed collapsible aortic valve," ASAIO Journal, Sep./ Oct. 1996, 42(5):M381-M385.
Orton, C., "Mitralseal: Hybrid Transcatheter Mitral Valve Replacement," Retrieved from the Internet: <http:/www.acvs.org/symposium/proceedings2011/data/papers/102.pdf>, pp. 311-312.
Pavcnik, D. et al. "Development and Initial Experimental Evaluation of a Prosthetic Aortic Valve for Transcatheter Placement," Radiology, 1992; 183:151-154.
Porstmann, W. et al., "Der Verschluß des Ductus Arteriosus Persistens ohne Thorakotomie," Thoraxchirurgie Vaskulare Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196(11):173-174.
Rashkind, W. J., "Historical Aspects of Interventional Cardiology: Past, Present, Future," Texas Heart Institute Journal, Dec. 1986, 13(4):363-367.
Reul, H. et al., "The Geometry of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Intery Radiol., Jul. 2003, 4:841-853.
Ross, D. N., "Aortic Valve Surgery," Guy's Hospital, London, 1968, pp. 192-197.
Rousseau, E. P. M. et al., "A mechanical analysis of the closed Hancock heart valve prosthesis," Journal of Biomechanics, 1988, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.

(56) References Cited

OTHER PUBLICATIONS

Selby, J. B., "Experience with New Retrieval Forceps for Foreign Body Removal in the Vascular, Urinary, and Biliary Systems," Radiology, 1990, 176:535-538.

Serruys, P. W. et al., "Stenting of Coronary Arteries. Are we the Sorcerer's Apprentice?," European Heart Journal, Sep. 1989, 10(9):774-782.

"Shape Memory Alloys," Retrieved from the Internet: <http://webdocs.cs.ualberta.ca/~database/MEMS/sma.html>, Feb. 5, 2016, 3 pages.

Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.

Tofeig, M. et al., "Transcatheter Closure of a Mid-Muscular Ventricular Septal Defect with an Amplatzer VSD Occluder Device," Heart, 1999, 81:438-440.

Uchida, B. T. et al., "Modifications of Gianturco Expandable Wire Stents," Am. J. Roentgenol., May 1988, 150(5):1185-1187.

Watt, A. H. et al., "Intravenous Adenosine in the Treatment of the Supraventricular Tachycardia; a Dose-Ranging Study and Interaction with Dipyridamole," British Journal of Clinical Pharmacology, 1986, 21:227-230.

Webb, J. G. et al., "Percutaneous Aortic Valve Implantation Retrograde from the Femoral Artery," Circulation, 2006, 113:842-850.

Wheatley, D. J., "Valve Prostheses," Rob & Smith's Operative Surgery, Fourth Edition, 1986, pp. 415-424, Butterworths.

Yoganathan, A. P. et al., "The Current Status of Prosthetic Heart Valves," In Polymetric Materials and Artificial Organs, American Chemical Society, 1984, pp. 111-150.

\* cited by examiner

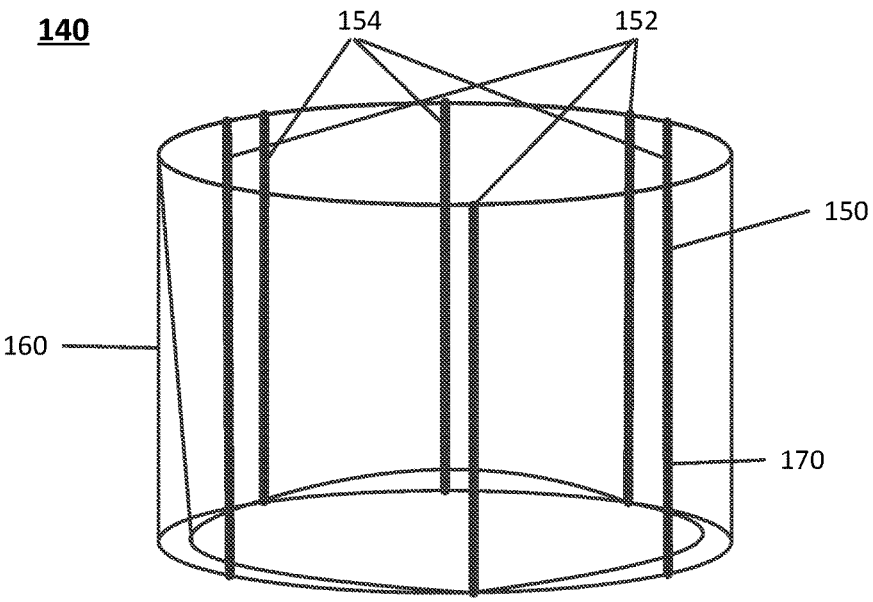
FIG. 2A
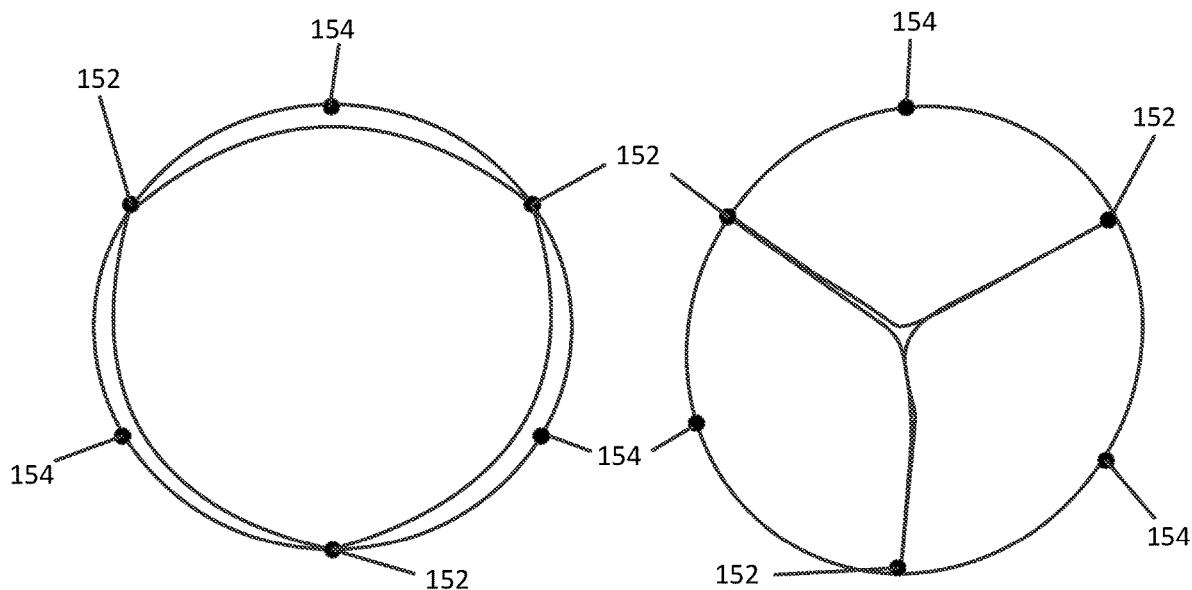
FIG. 2B  FIG. 2C

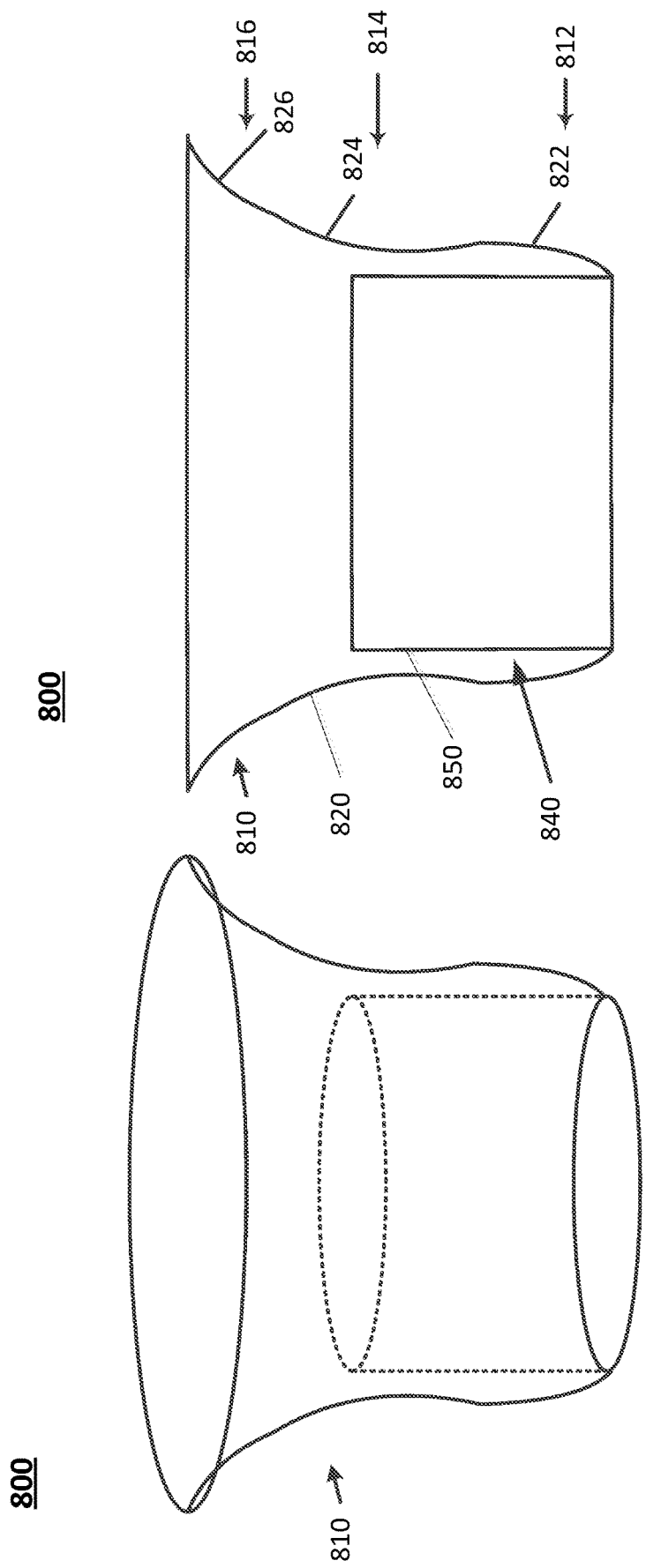

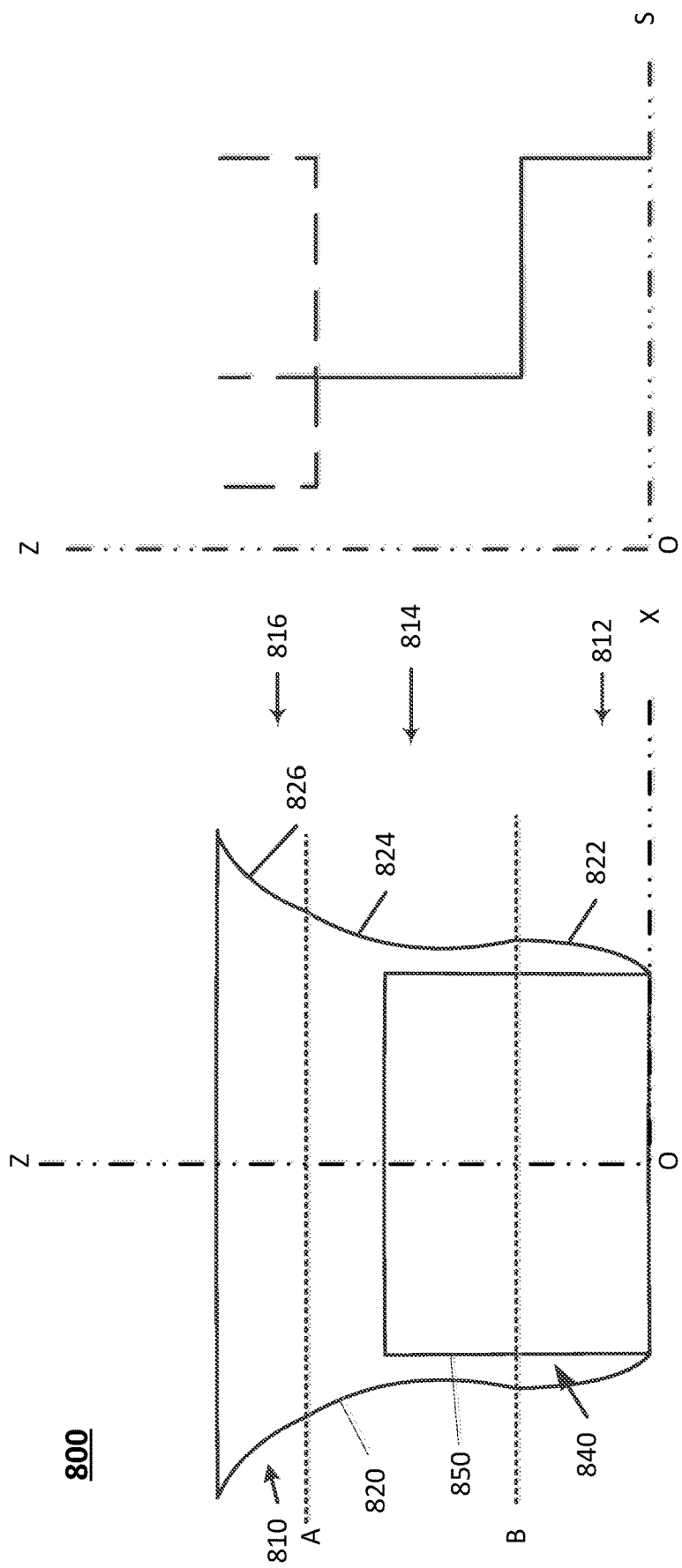

THROMBUS MANAGEMENT AND STRUCTURAL COMPLIANCE FEATURES FOR PROSTHETIC HEART VALVES

CROSS-REFERENCE TO RELATED APPLICATIONS

This application is a divisional of U.S. Pat. No. 9,597,181, filed Dec. 21, 2015, which is a continuation of International Application No. PCT/US2014/044047, filed Jun. 25, 2014, which is a continuation-in-part of U.S. patent application Ser. No. 14/155,535, filed Jan. 15, 2014, and claims priority to and the benefit of U.S. Provisional Application No. 61/839,237, filed Jun. 25, 2013 and U.S. Provisional Application No. 61/840,313, filed Jun. 27, 2013. Each of the disclosures of the foregoing applications is incorporated herein by reference in its entirety.

BACKGROUND

Prosthetic heart valves, including those for insertion into atrioventricular valves (tricuspid and mitral valves) are susceptible to various problems, including problems with insufficient articulation and sealing of the valve within the native valve annulus, pulmonary edema due to poor atrial drainage, perivalvular leaking around the install prosthetic valve, lack of a good fit for the prosthetic valve within the native valve annulus, atrial tissue erosion, excess wear on the Nitinol structures, interference with the aorta at the posterior side of the mitral annulus, lack of customization, and thrombus formation, to name a few. Accordingly, there is still a need for a prosthetic heart valve that can address some or all of these problems.

SUMMARY

A prosthetic heart valve can include an outer support assembly, an inner valve assembly, which define between them an annular space, and a pocket closure that bounds the annular space to form a pocket in which thrombus can be formed and retained. A prosthetic heart valve can alternatively, or additionally, include an outer support assembly and an inner valve assembly, coupled at the ventricle ends of the outer support assembly and the inner valve assembly, with the outer support assembly being relatively more compliant in hoop compression in a central, annulus portion than at the ventricle end, so that the prosthetic valve can seat securely in the annulus while imposing minimal loads on the inner valve assembly that could degrade the performance of the valve leaflets.

BRIEF DESCRIPTION OF THE DRAWINGS

FIGS. 2A-C are schematic views of an inner valve assembly of the prosthetic heart valve of FIGS. 1A and 1B.

FIGS. 27 and 28 are schematic perspective and side cross sectional views of a prosthetic heart valve according to another embodiment.

FIGS. 29A-D are schematic illustrations of stiffness profiles of a prosthetic heart valve according to another embodiment.

DETAILED DESCRIPTION

Figure 1A:
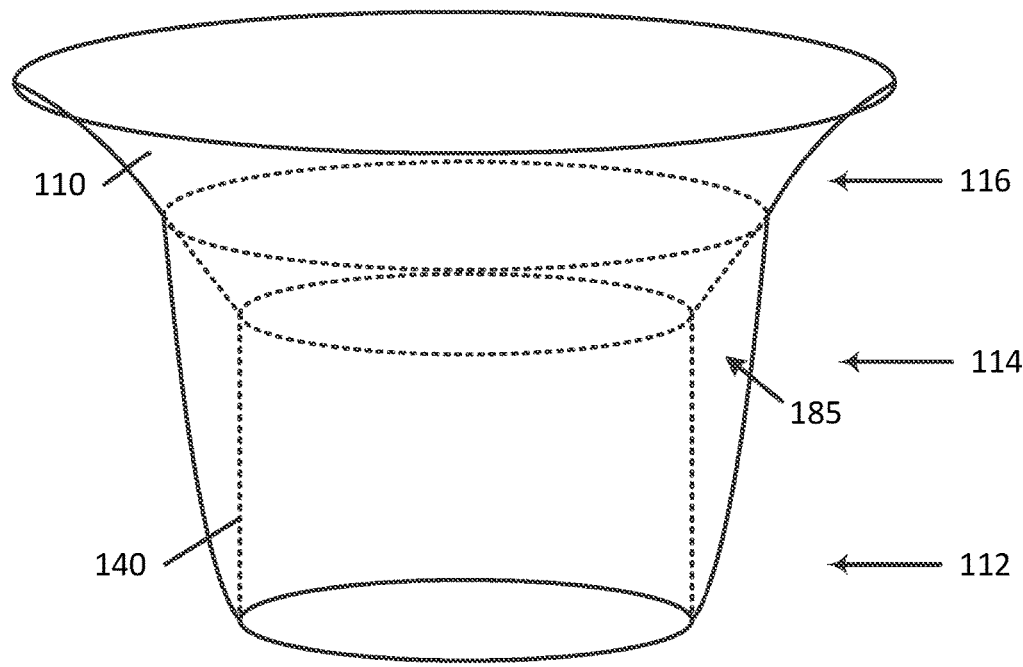
FIGS. 1A and 1B are schematic perspective and side cross sectional views of a prosthetic heart valve according to an embodiment.
Figure 1B:
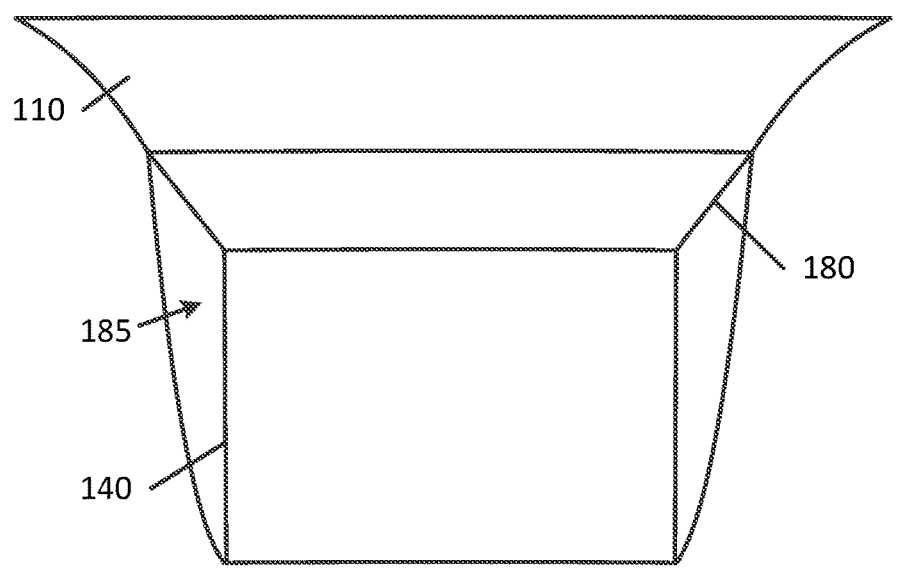

A schematic representation of a prosthetic heart valve 100 is shown in FIGS. 1A and 1B. Prosthetic heart valve 100 is designed to replace a damaged or diseased native heart valve such as a mitral valve. Valve 100 includes an outer frame assembly 110 and an inner valve assembly 140 coupled to the outer frame assembly.

Although not separately shown in the schematic illustration of outer frame assembly 110 in FIGS. 1A and 1B, outer fame assembly 110 may be formed of an outer frame 120, covered on all or a portion of its outer face with an outer covering 130, and covered on all or a portion of its inner face by an inner covering 132.

Outer frame 120 can provide several functions for prosthetic heart valve 100, including serving as the primary structure, as anchoring mechanism and/or an attachment point for a separate anchoring mechanism to anchor the valve to the native heart valve apparatus, a support to carry inner valve assembly 140, and/or a seal to inhibit paravalvular leakage between prosthetic heart valve 100 and the native heart valve apparatus.

Outer frame 120 is preferably formed so that it can be deformed (compressed and/or expanded) and, when released, return to its original (undeformed) shape. To achieve this, outer frame 120 is preferably formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may be used.

Outer frame 120 is preferably formed from a laser cut, thin-walled tube of Nitinol®. The laser cuts form regular cutouts in the thin Nitinol® tube. The tube can be expanded radially, placed on a mold or mandrel of the desired shape, heated to the martensitic temperature, and quenched. The treatment of the frame in this manner will form an open lattice frame structure, and may have a flared end or cuff at the atrium end portion 126 of outer frame 120. Outer frame 120 thus has shape memory properties and will readily revert to the memory shape at the calibrated temperature. Alternatively, outer frame 120 may be constructed from braided wire or other suitable material.

Inner valve assembly 140 is shown schematically in more detail in FIGS. 2A-2C. Inner valve assembly 140 can include an inner frame 150, an outer covering 160, and leaflets 170. In the simplified form shown schematically in FIG. 2A, inner frame 150 includes six axial posts or frame members that support outer covering 160 and leaflets 170. Leaflets 170 are attached along three of the posts, shown as commissure posts 152 in FIG. 2A, and outer covering 160 is attached to the other three posts, 154 in FIG. 2A, and optionally to commissure posts 152. In the simplified form illustrated schematically in FIG. 2A, each of outer covering 160 and leaflets 170 are formed of approximately rectangular sheets of material, which are joined together at their upper, or atrium end. The lower, ventricle end of outer covering 160 may be joined to inner covering 132 of outer frame assembly 110 (not shown in FIG. 2A), and the lower, ventricle end of leaflets 170 may form free edges, though coupled to the lower ends of commissure posts 152.

As shown in FIGS. 2B and 2C, leaflets 170 are movable between an open configuration (FIG. 2B) and a closed configuration (FIG. 2C) in which the leaflets coapt, or meet in sealing abutment.

At the lower, or ventricle end, leaflets 170 may have a smaller perimeter than outer covering 160. Thus, the free lower edges of the leaflets, between commissure posts 152 (each portion of leaflets 170 between adjacent commissure posts being referred to as a "belly" of leaflets 170) are spaced radially from the lower edge of outer covering 160. This radial spacing facilitates movement of the leaflets from the open position in FIG. 2B to the closed position in FIG. 2C, as the counter flow of blood from the ventricle to the atrium during systole can catch the free edges of the bellies and push the leaflets closed.

Outer covering 130 and inner covering 132 of outer frame 120, outer covering 160 and leaflets 170 may be formed of any suitable material, or combination of materials. In some embodiments, the tissue is optionally a biological tissue, such as a chemically stabilized tissue from a heart valve of an animal, such as a pig, or pericardial tissue of an animal, such as cow (bovine pericardium) or sheep (ovine pericardium) or pig (porcine pericardium) or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old. Alternatively, valve leaflets 170 may optionally be made from pericardial tissue or small intestine submucosal tissue.

Synthetic materials, such as polyurethane or polytetrafluoroethylene, may also be used for valve leaflets 170. Where a thin, durable synthetic material is contemplated, e.g. for outer covering 130 or inner cover 132, synthetic polymer materials such expanded polytetrafluoroethylene or polyester may optionally be used. Other suitable materials may optionally include thermoplastic polycarbonate urethane, polyether urethane, segmented polyether urethane, silicone polyether urethane, silicone-polycarbonate urethane, and ultra-high molecular weight polyethylene. Additional biocompatible polymers may optionally include polyolefins, elastomers, polyethylene-glycols, polyethersulphones, polysulphones, polyvinylpyrrolidones, polyvinylchlorides, other fluoropolymers, silicone polyesters, siloxane polymers and/or oligomers, and/or polylactones, and block co-polymers using the same.

In another embodiment, valve leaflets 170 may optionally have a surface that has been treated with (or reacted with) an anti-coagulant, such as, without limitation, immobilized heparin. Such currently available heparinized polymers are known and available to a person of ordinary skill in the art.

As shown in FIGS. 1A, 1B, and 2A, inner valve assembly 140 may be substantially cylindrical, and outer frame assembly 110 may be tapered, extending from a smaller diameter (slightly larger than the outer diameter of inner valve assembly 140) at a lower, ventricle portion 112 (where it is coupled to inner valve assembly 140) to a larger diameter, atrium portion 116, with an intermediate diameter, annulus portion 114 between the atrium and ventricle portions.

A tapered annular space or pocket 185 is thus formed between the outer surface of inner valve assembly 140 and the inner surface of outer frame assembly 110, open to the atrium end of valve assembly 100. When valve assembly 100 is disposed in the annulus of a native heart valve, blood from the atrium can move in and out of pocket 185. The blood can clot, forming thrombus, and the thrombus can be washed out by the flow of blood during the cyclic pumping of the heart, which is undesirable. To inhibit such washout of thrombus, and to enhance clotting, ingrowth of tissue into the surfaces of valve 100, and produce other benefits, the pocket can be covered, or enclosed, by a pocket closure 180.

Pocket closure 180 can be formed at least in part of any suitable material that is sufficiently porous to allow blood, including particularly red blood cells, to enter pocket 185, but is not so porous as to allow undesirably large thrombi to leave the pocket 185, or to allow washout of thrombus formed in the pocket 185. For example, pocket closure 180 may be formed at least in part from a woven or knit polyester fabric with apertures less than 160μ, and preferably between 90μ and 120μ. It is not necessary for the entirety of pocket closure 180 to be formed of the same material, with the same porosity. For example, some portions of pocket closure 180 may be formed of a less porous, or blood impermeable, material and other portions formed of material of the porosity range noted above. It is also contemplated that a portion of the outer frame assembly 110 or the inner valve assembly 140 may be formed with an aperture that communicates with pocket 180, covered by a closure formed of material having the desired porosity, thus providing another path by which blood may enter, but thrombi are prevented from leaving, atrial pocket 185.

The outer surface of inner valve assembly 110, and/or the inner surface of outer frame assembly 140, need not by circular in cross-section as shown schematically in FIGS. 1A and 1B, but may be of non-constant radius at a given location along the central axis of valve 100. Thus, pocket 185 may not be of constant cross-section, and may not be continuous, but rather may be formed in two or more fluidically isolated, partially annular volumes. Similarly, pocket closure 180 need not be shaped as a ring with constant width as shown schematically in FIGS. 1A and 1B, but rather than be a continues ring of varying with, a more complicated continuous shape, or may be formed in multiple, discrete sections.

Pocket closure 180 serves to trap and/or slow the flow of blood within pocket 185, reducing hemodynamic washout and increasing formation of thrombus in pocket 185. It also promotes active in-growth of native tissue into the several coverings of prosthetic heart valve 100, further stabilizing valve 100 in the native heart valve. The material forming the outer covering of inner valve assembly 140 can also be hardened or stiffened, providing better support for leaflets 170. Also, a mass of thrombus filling pocket 185 can serve as potting for inner valve assembly 140, further stabilizing the valve assembly. Greater stability for inner valve assembly 140 can provide more reliable coaption of valve leaflets 170, and thus more effective performance. The mass of thrombus can also stabilize the outer frame assembly 110 after it has been installed in, and flexibly conformed to, the native valve apparatus. This can provide a more effective seal between prosthetic heart valve 100 and the native valve apparatus, and reduce perivalvular leakage.

Figure 3:
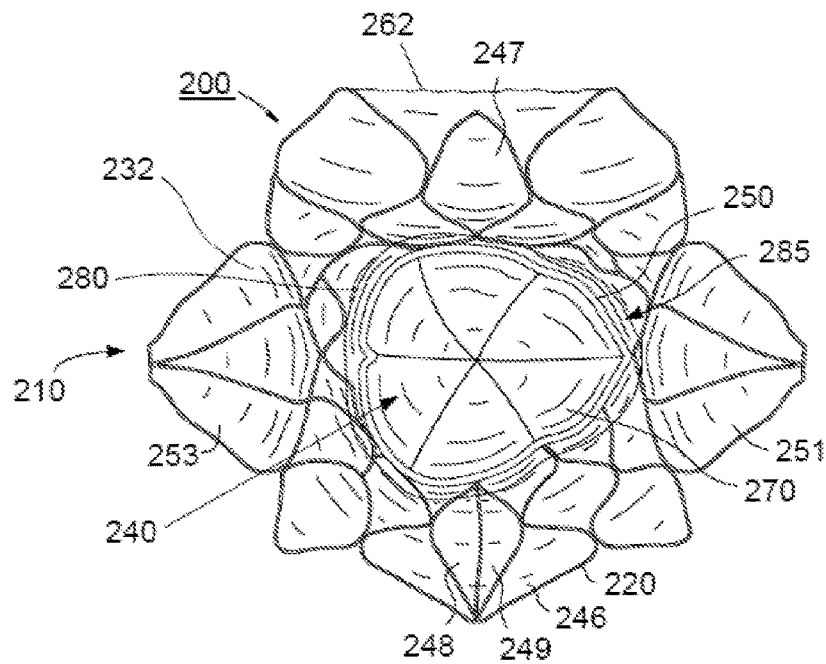
FIG. 3 is a top view of a prosthetic heart valve according to another embodiment.

One possible implementation of the prosthetic heart valve shown schematically in FIGS. 1A-2C is prosthetic heart valve 200, shown in top view in FIG. 3. Prosthetic heart valve 200 includes an outer frame assembly 210 and an inner valve assembly 240 coupled to the outer frame assembly.

The outer frame assembly 210 includes an outer frame 220, covered on all or a portion of its outer face with an outer covering 230 (not visible), and covered on all or a portion of its inner face by an inner covering 232.

The inner valve assembly 240 includes an inner frame 250, an outer covering 260 (not visible), and leaflets 270. Inner frame 250 includes six axial posts or frame members that support outer covering 260 and leaflets 270. The inner valve assembly 240 may be substantially cylindrical, and outer frame assembly 210 may be tapered, extending from a smaller diameter (slightly larger than the outer diameter of inner valve assembly 240) at a lower, ventricle portion (where it is coupled to inner valve assembly 240) to a larger diameter, atrium portion, with an intermediate diameter, annulus portion between the atrium and ventricle portions.

A tapered annular space or pocket 285 (e.g., atrial thrombogenic sealing pocket) is thus formed between the outer surface of inner valve assembly 240 and the inner surface of outer frame assembly 210, open to the atrium end of valve assembly 200. The pocket closure 280 can, for example, be formed from a circular piece of wire, or halo, with a permeable mesh fabric or tissue, that is sewn and thereby connected to the inner frame 250 and/or to the leaflets 170. The inner frame 250 has an inner wireframe structure (e.g., made of Nitinol wire) that supports the leaflets 270 sewn to the inner frame 250 and functions as a valve. The inner frame 250 in FIG. 3 includes three U-shaped wire components joined at their opened ends to form junctions. Leaflets 270 are sewn to these components to form articulating leaflets 170 creating and functioning as a prosthetic valve (e.g., prosthetic tricuspid valve; prosthetic mitral valve; prosthetic aortic valve, etc.).

Moreover, the inner frame 250 has (tether) attachment apertures 211 (not shown), for attaching tether assembly 290 (not shown). Tether assembly 290 is connected to epicardial securing pad 254 (not shown).

In operation, the inner valve assembly 240 is disposed within and secured within the outer frame assembly 210. Outer frame assembly 210 may also have in various embodiments an outer stent tissue material. Outer frame assembly 210 includes an articulating collar 246 which has a collar cover 248. Articulating collar 246 is specifically shaped to solve leakage issues arising from native structures. In particular, collar 246 is composed of an A2 segment 247, a P2 segment 249, and two commissural segments, the A1-P1 segment 251, and the A3-P3 segment 253. The collar 246 may also have in preferred embodiments a shortened or flattened or D-shaped section 262 of the A2 segment in order to accommodate and solve left ventricular outflow tract (LVOT) obstruction issues.

In operation, the prosthetic heart valve 200 may be deployed (e.g., as a prosthetic mitral valve) using catheter delivery techniques. The prosthetic heart valve 200 is compressed within a narrow catheter and delivered to the annular region of the native valve (e.g., the left atrium) with a pre-attached tether assembly 290. There, the valve 200 is pushed out of the catheter where it springs open into its pre-formed functional shape without the need for manual expansion (e.g., manual expansion using an inner balloon catheter). When the valve 200 is pulled into place, the outer frame assembly 210 is seated in the native mitral annulus, leaving the articulating collar 246 to engage the atrial floor and prevent pull-thru (where the valve 200 is pulled into the ventricle). In such embodiments, it is not necessary to cut-away the native leaflets, as has been taught in prior prosthetic efforts. Instead, the native leaflets can be used to provide a tensioning and/or sealing function around the outer frame assembly 210. It is advantageous for the valve 200 to be asymmetrically deployed in order to address LVOT problems where non-accommodating prosthetic valves push against the A2 anterior segment of the valve (e.g., mitral valve) and close blood flow through the aorta, which anatomically sits immediately behind the A2 segment of the mitral annulus. Thus, D-shaped section 262 is deployed substantially immediately adjacent/contacting the A2 segment since the flattened D-shaped section 262 is structurally smaller and has a more vertical profile (closer to paralleling the longitudinal axis of the outer frame assembly 212) and thereby provides less pressure on the A2 segment. Once the valve 200 is properly seated, tether assembly 290 may be extended out through the apical region of the left ventricle and secured using an epicardial pad 254 or similar suture-locking attachment mechanism (not shown).

In an alternate embodiment, the tether assembly 290 is on the outer frame assembly 210, which would then have (tether) attachment apertures 213 for attaching tether assembly 290 to epicardial securing pad 254.

Figure 4:
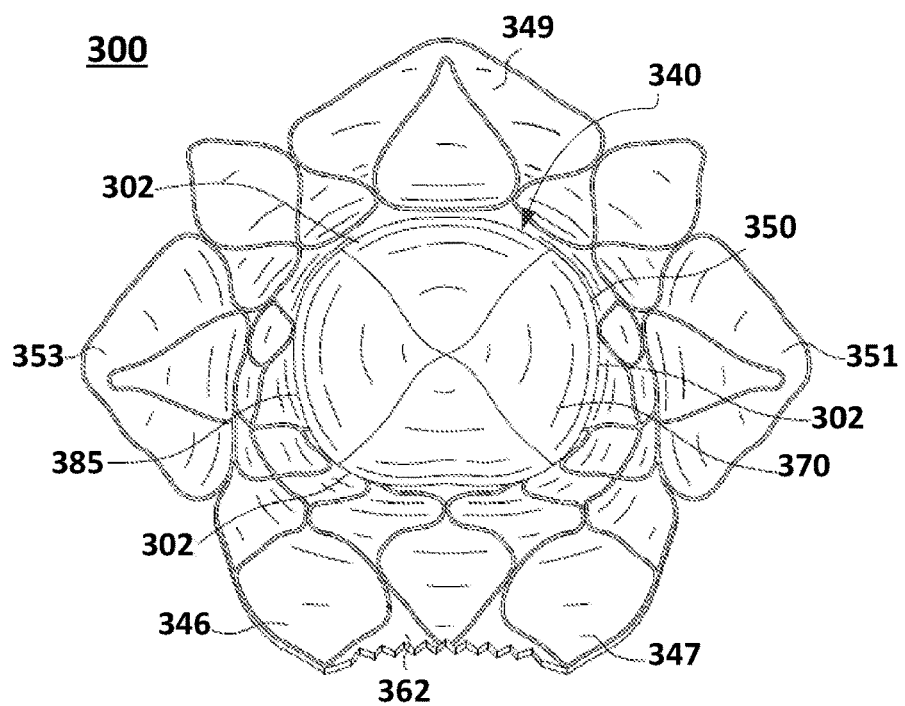
FIG. 4 is a top view of a prosthetic heart valve according to another embodiment.

FIG. 4 is a top, or atrial, view of another embodiment of a prosthetic heart valve 300, illustrated without pocket closure 380. FIG. 4 shows the top of the junction tip 302 of the three U-shaped wire components of inner frame 350 joined at their opened ends to form junctions 302. Leaflets 370 are sewn to these components to form articulating leaflets 370 creating and functioning as a prosthetic valve (e.g., prosthetic tricuspid valve, prosthetic mitral valve, prosthetic aortic valve, etc.). Thrombogenic pocket 385 is shown below the plane of the collar. FIG. 4 shows vertical A2 segment 347, the P2 segment 349, and the commissural A1-P1 segment 351 and A3-P3 segment 353. FIG. 4 shows how upon deployment blood would fill the void or gap 385 between the inner valve assembly 340 and the outer frame assembly 310 of the valve 300. This blood creates a temporary fluid seal that pools in that space and provide a pressure buffer against the leakage inducing forces that accompany systolic and diastolic related intra-atrial and intra-ventricular pressure. Moreover, FIG. 4 provides an illustration of collar 346 that may, in some embodiments, include a shortened or flattened or D-shaped section 362 of the A2 segment in order to accommodate and solve left ventricular outflow tract (LVOT) obstruction issues.

Figure 5:
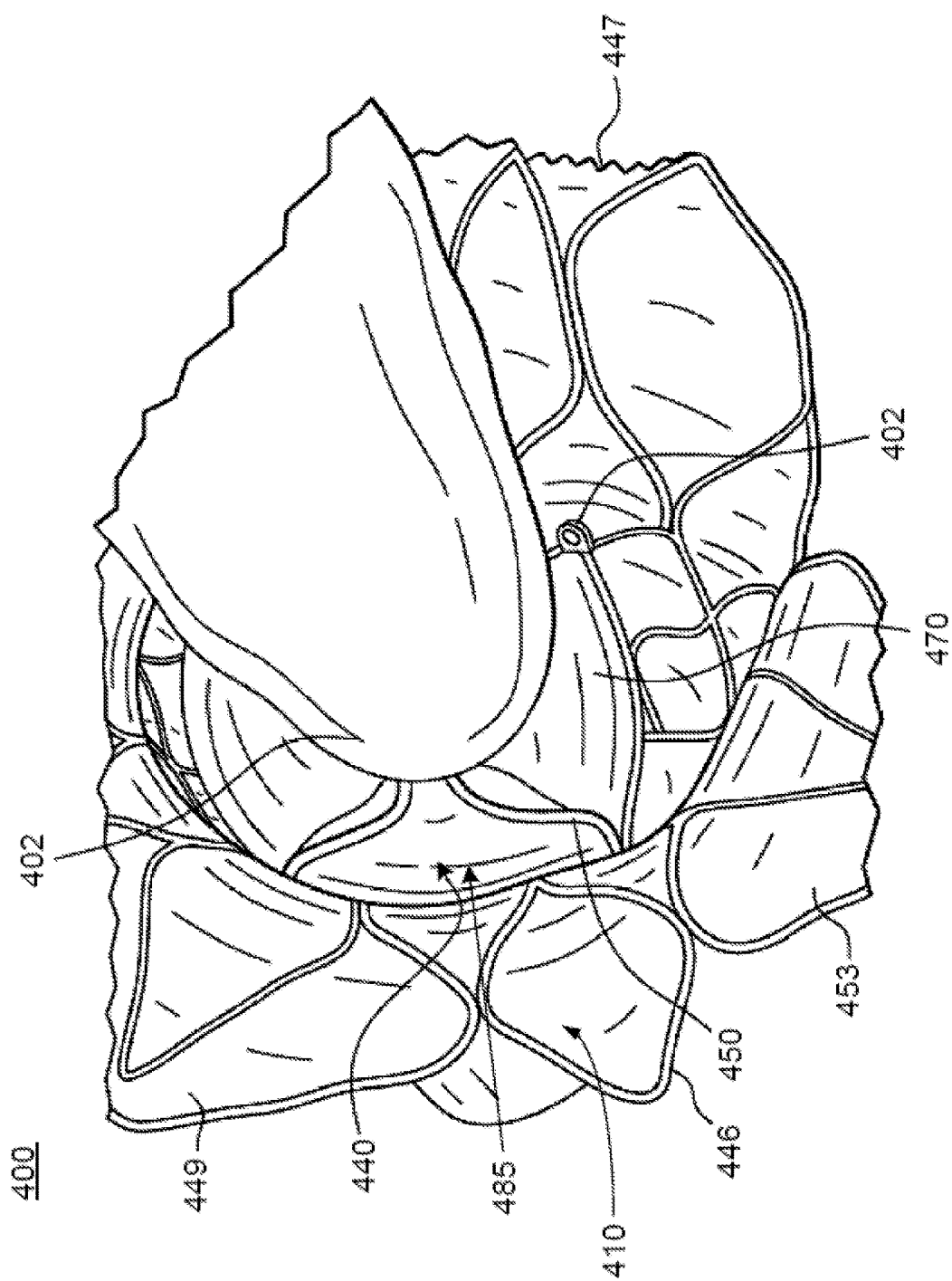
FIG. 5 is a perspective side view of a portion of a prosthetic heart valve according to another embodiment.

FIG. 5 is a perspective side view of the P2 area 447 and A3-P3 area 453 of a self-expanding pre-configured compressible transcatheter prosthetic cardiovascular valve 400 contemplated herein, that contains as a sub-component, a self-expanding inner valve assembly 440. The valve 400 further includes as a sub-component, an outer frame assembly 410. The outer frame assembly 410 and the inner valve assembly 440 collectively define thrombogenic pockets 485. FIG. 5 shows one of the three U-shaped wire components of inner frame 450 joined at their opened ends to form junctions 402. Leaflets 470 are sewn to these components to form articulating leaflets 470 creating and functioning as a prosthetic valve. Thrombogenic pocket 485 is shown slightly below the plane of the majority of collar 446 except for the vertical A2 segment 447, the P2 segment 449, and the commissural A1-P1 segment 451 (not shown) and A3-P3 segment 453. FIG. 5 shows how upon deployment blood would fill the void or gap (i.e., pocket 485) between the inner valve assembly 440 and the outer frame assembly 410 at the A3-P3 segment 453 area of the valve 400. This blood creates a temporary fluid seal that would pool in that space and provide a pressure buffer against the leakage inducing forces that accompany systolic and diastolic related intra-atrial and intra-ventricular pressure.

Figure 6:
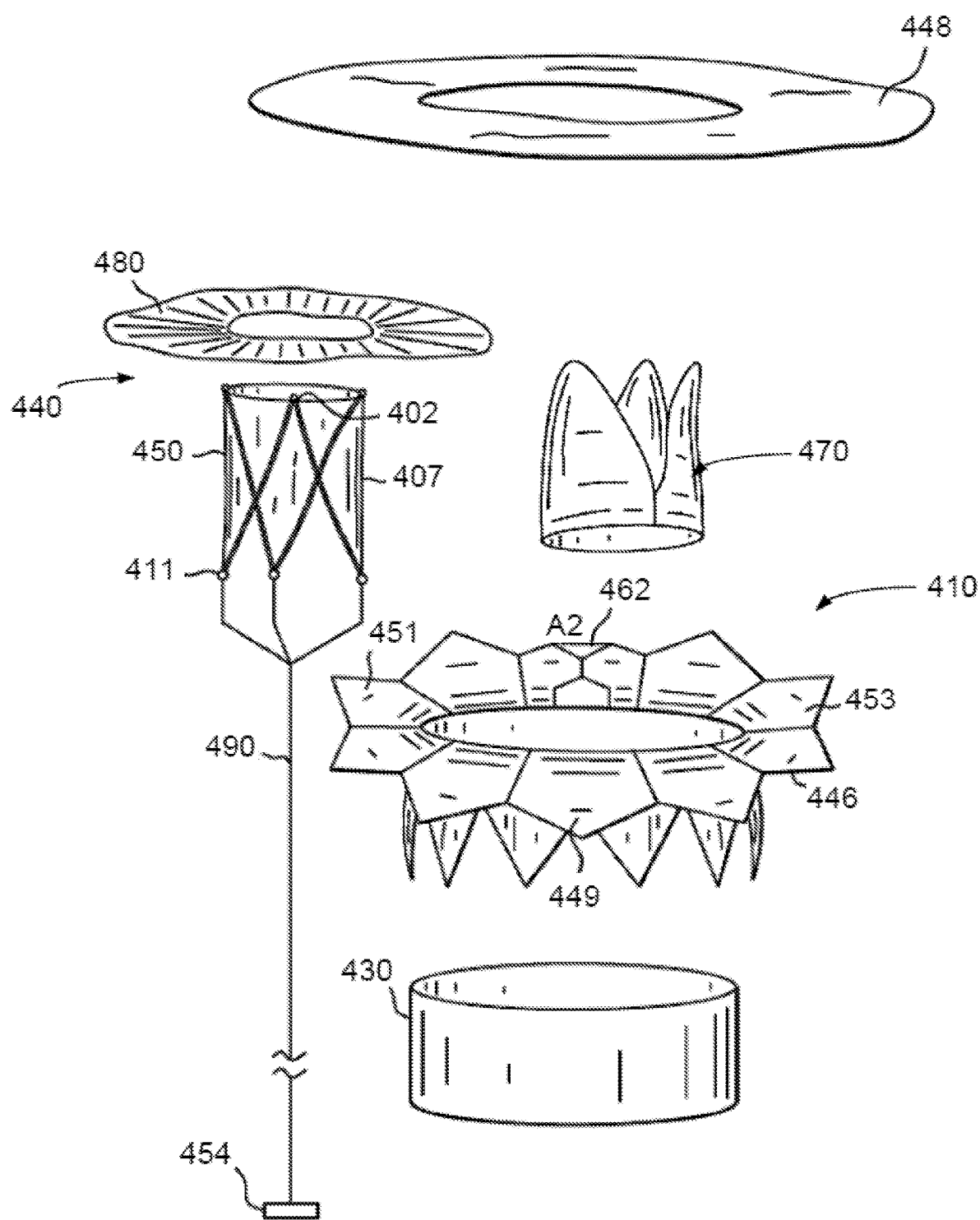
FIG. 6 is an exploded view of a prosthetic heart valve system according to another embodiment.

FIG. 6 is an exploded view of an embodiment of the pre-configured compressible transcatheter prosthetic cardiovascular valve 400, which contains as a sub-component, a self-expanding inner frame 450. The valve 400 further includes as a sub-component, an outer frame assembly 410. The outer frame assembly 410 and the inner valve assembly 440 collectively define thrombogenic pockets 485 (not shown). The pocket 485 is formed between inner valve assembly 440, as the inside of the V-shaped or U-shaped pocket, and the outer frame assembly 410 with outer covering 430, as the outside of the V-shaped or U-shaped pocket. In this valve 400, the inner valve assembly 440 has an atrial thrombogenic sealing pocket closure 480 (not shown) (e.g., formed from a circular piece of wire, or halo), with a permeable mesh fabric or tissue, that is sewn and thereby connected to the inner frame 450 and/or to the leaflets 470. The inner frame 450 includes an inner wire-frame structure made of Nitinol wire that supports leaflets 570 sewn to the inner frame 450 and functions as a valve. The inner frame 450 includes three main U-shaped wire components 407 joined at their opened ends to form junctions 402. Optionally, in some embodiments, the inner frame 450 can include additional wire cross-members or struts (e.g., more than three).

In this valve 400, the inner frame 450 is sewn with tissue and acts a cover to prevent valvular leakage. The inner valve assembly 440 includes the leaflets 470. The leaflets 470 include articulating leaflets that define a valve function. The leaflets 470 are sewn to the inner frame 450. The inner frame 450 also has (tether) attachment apertures 411 for attaching tether assembly 490. Tether assembly 490 is shown in this example as connected to epicardial securing pad 454. In operation, the covered inner valve assembly 440 (with leaflets 470), is disposed within and secured within the outer frame assembly 410. Outer frame assembly 410 may also have in various embodiments an outer covering 460. Outer frame assembly 410 has an articulating collar 446 which has a collar cover 448. Articulating collar 446 may also have in preferred embodiments a flattened or D-shaped section 462 at the A2 area to accommodate and solve left ventricular outflow tract (LVOT) obstruction issues. Collar 446 may also have specially formed commissural segments to prevent commissural leakage at A1-P1 segment 451 and at A3-P3 segment 453

In operation, the valve 400 may be deployed as a prosthetic valve using catheter delivery techniques. The valve 400 is compressed within a narrow catheter and delivered to the annular region of the native valve (e.g., the left atrium) with a pre-attached tether assembly 490. There, the valve 400 is pushed out of the catheter where it springs open into its pre-formed functional shape without the need for manual expansion (e.g., manual expansion using an inner balloon catheter). When the valve 400 is pulled into place, the outer frame assembly 410 is seated in the native annulus (e.g., native mitral annulus), leaving the articulating collar 446 to engage the atrial floor and prevent pull-thru (where the valve is pulled into the ventricle). In such embodiments, it is not necessary to cut-away the native leaflets, as has been taught in prior prosthetic efforts. Instead, the native leaflets can be used to provide a tensioning and/or sealing function around the valve 400 (e.g., around the outer frame assembly 410). It is advantageous for the valve 400 to be asymmetrically deployed in order to address LVOT problems where non-accommodating prosthetic valves push against the A2 anterior segment of the valve (e.g., the mitral valve) and close blood flow through the aorta, which anatomically sits immediately behind the A2 segment of the annulus (e.g., mitral annulus).

Thus, D-shaped section 462 is deployed substantially immediately adjacent/contacting the A2 segment since the flattened D-shaped section 462 is structurally smaller and has a more vertical profile (closer to paralleling the longitudinal axis of the outer frame assembly 410) and thereby provides less pressure on the A2 segment. Once the valve 400 is properly seated, tether assembly 490 may be extended out through the apical region of the left ventricle and secured using an epicardial pad 454 or similar suture-locking attachment mechanism.

Figure 7:
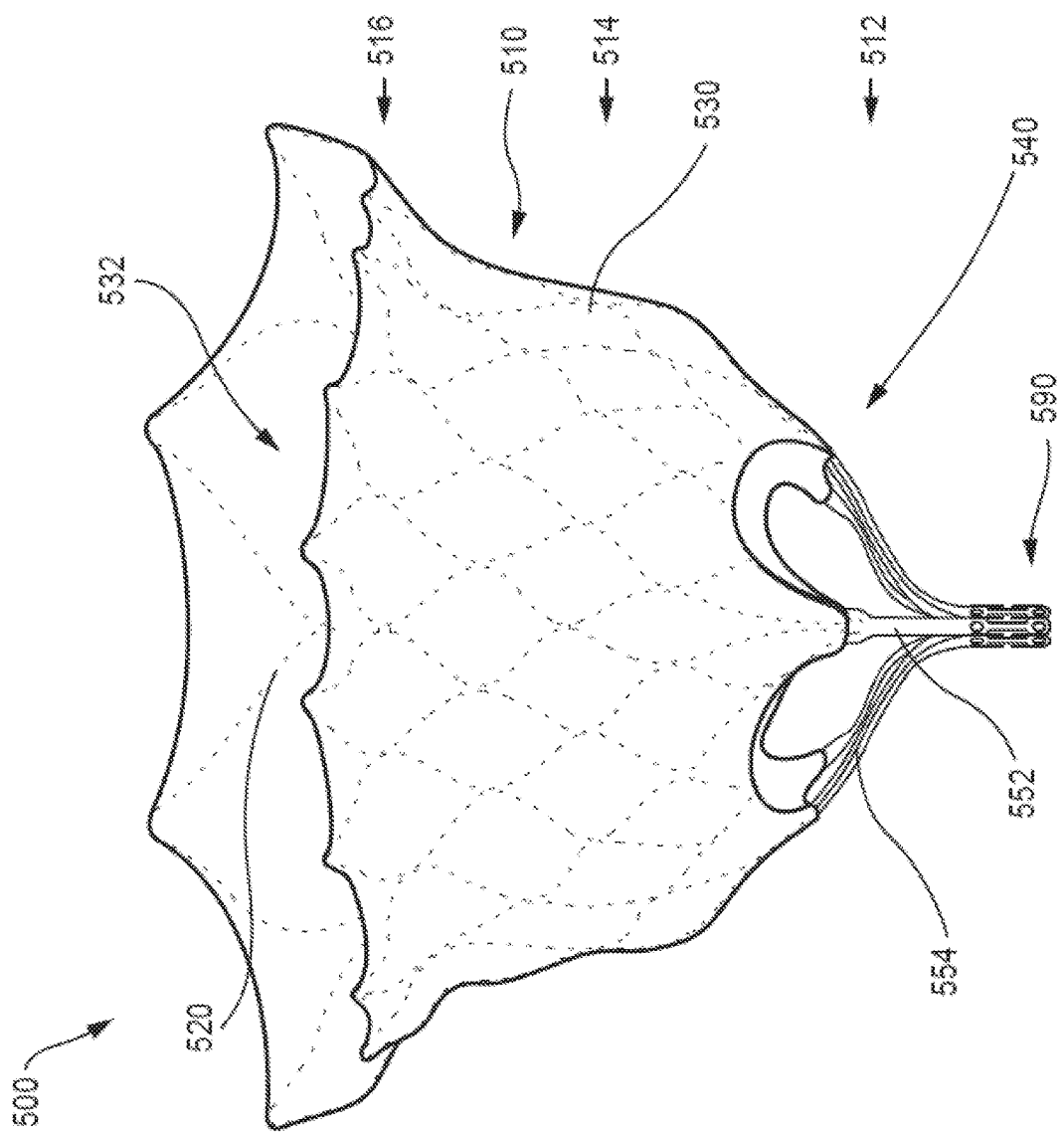
FIGS. 7-9 are front, bottom, and top views of a prosthetic heart valve according to another embodiment.
Figure 8:
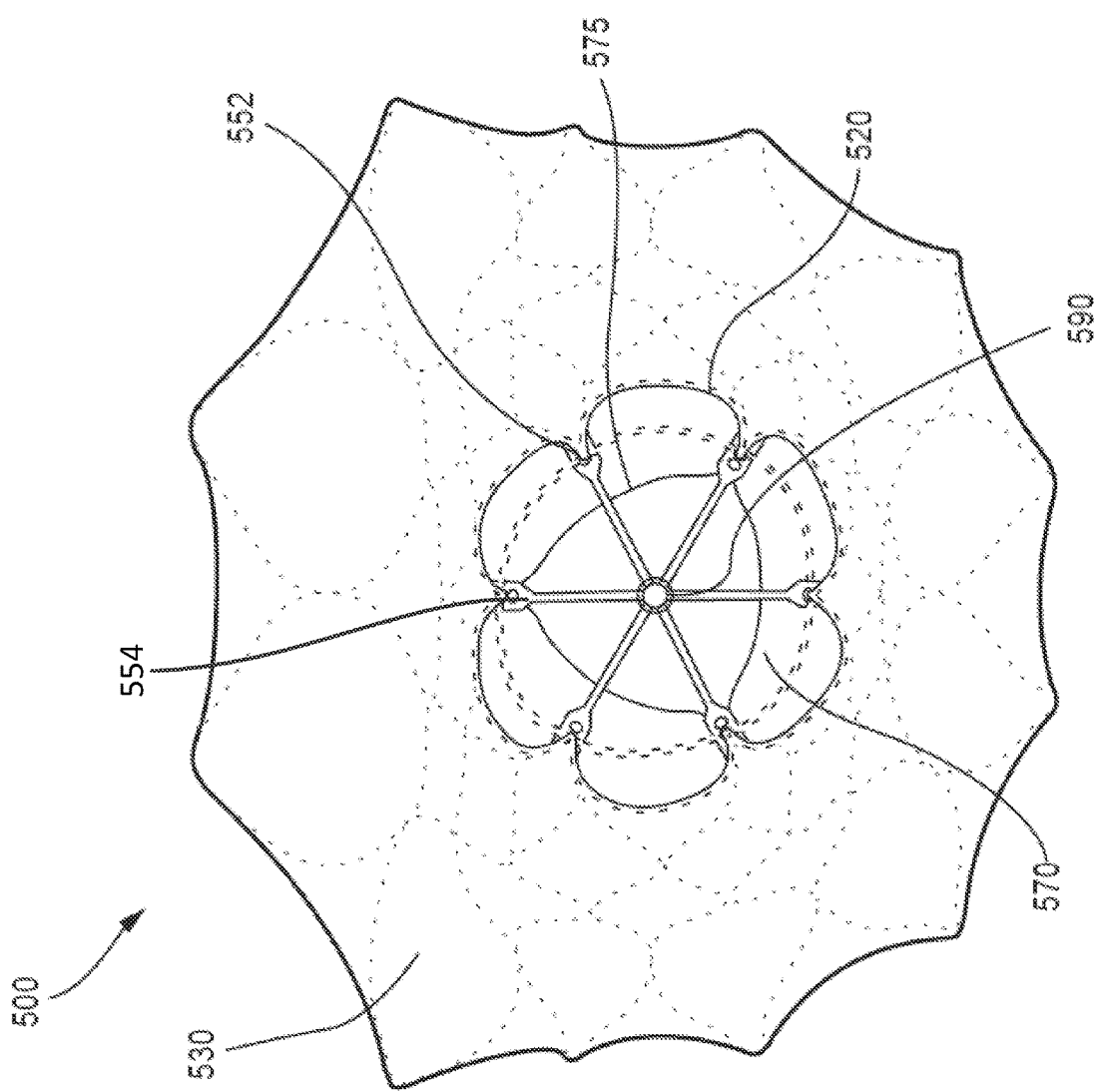
Figure 9:
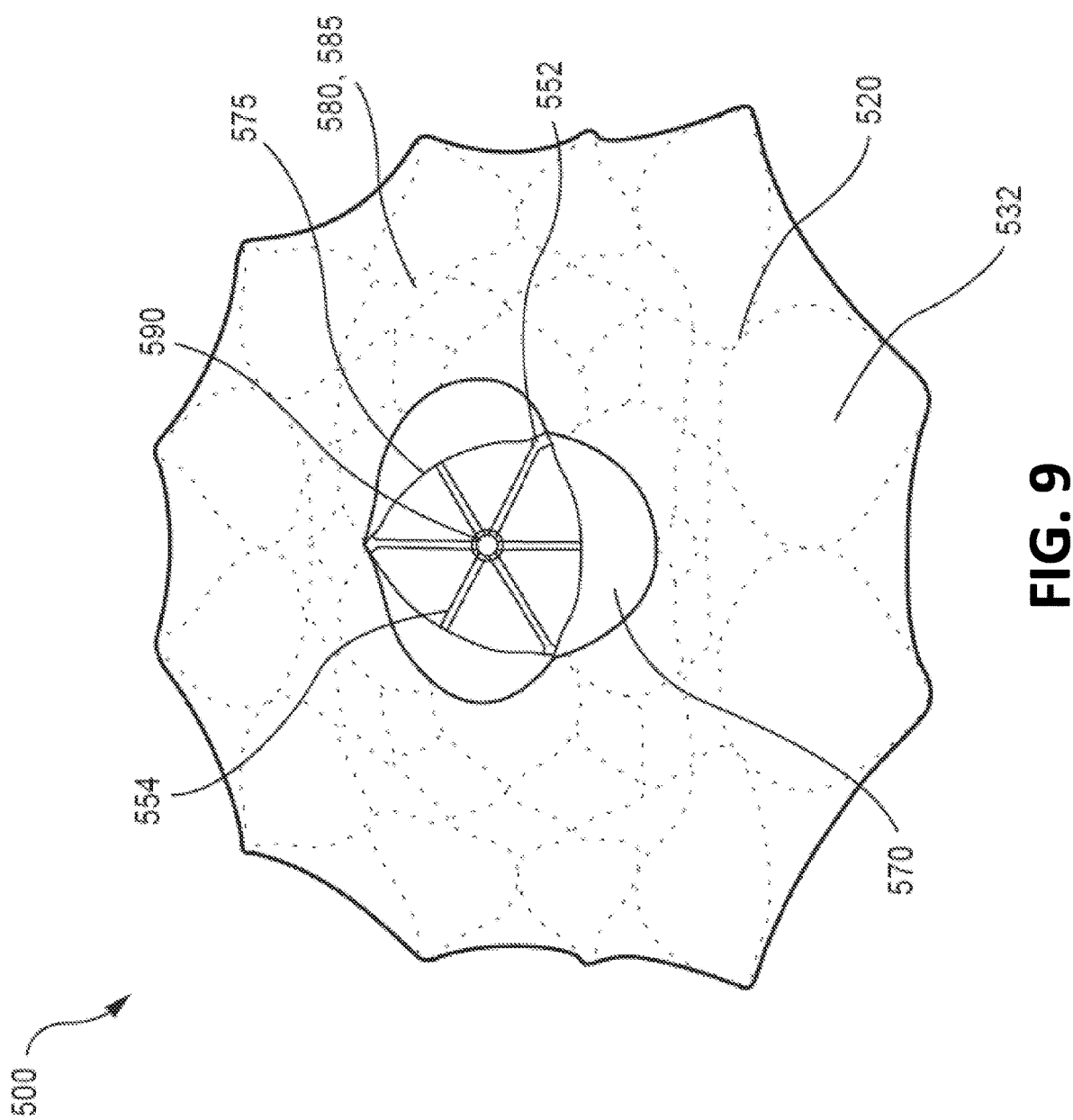

FIGS. 7-9 are front, bottom, and top views, respectively, of a prosthetic heart valve 500 according to an embodiment.

Prosthetic heart valve 500 is designed to replace a damaged or diseased native heart valve such as a mitral valve. Valve 500 includes an outer frame assembly 510 and an inner valve assembly 540 coupled to the outer frame assembly 510.

As shown, outer frame assembly 510 includes an outer frame 520, covered on all or a portion of its outer face with an outer covering 530, and covered on all or a portion of its inner face by an inner covering 532.

Outer frame 520 can provide several functions for prosthetic heart valve 500, including serving as the primary structure, as anchoring mechanism and/or an attachment point for a separate anchoring mechanism to anchor the valve to the native heart valve apparatus, a support to carry inner valve assembly 540, and/or a seal to inhibit paravalvular leakage between prosthetic heart valve 500 and the native heart valve apparatus.

Outer frame 520 is configured to be manipulated and/or deformed (e.g., compressed and/or expanded) and, when released, return to its original (undeformed) shape. To achieve this, outer frame 520 can be formed of materials, such as metals or plastics, that have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may be used.

As best shown in FIG. 7, outer frame assembly 510 has an upper end (e.g., at the atrium portion 516), a lower end (e.g., at the ventricle portion 512), and a medial portion (e.g., at the annulus portion 514) therebetween. The medial portion of the outer frame assembly 510 has a perimeter that is configured (e.g., sized, shaped) to fit into an annulus of a native atrioventricular valve. The upper end of the outer frame assembly 510 has a perimeter that is larger than the perimeter of the medial portion. In some embodiments, the perimeter of the upper end of the outer frame assembly 510 has a perimeter that is substantially larger than the perimeter of the medial portion. As shown best in FIG. 9, the upper end and the medial portion of the outer frame assembly 510 has a D-shaped cross-section. In this manner, the outer frame assembly 510 promotes a suitable fit into the annulus of the native atrioventricular valve.

Inner valve assembly 540 includes an inner frame 550, an outer covering 560, and leaflets 570. As shown, the inner valve assembly 540 includes an upper portion having a periphery formed with multiple arches. The inner frame 550 includes six axial posts or frame members that support outer covering 560 and leaflets 570. Leaflets 570 are attached along three of the posts, shown as commissure posts 552 (best illustrated in FIG. 8), and outer covering 560 is attached to the other three posts, 554 (best illustrated in FIG. 8), and optionally to commissure posts 552. Each of outer covering 560 and leaflets 570 are formed of approximately rectangular sheets of material, which are joined together at their upper, or atrium end. The lower, ventricle end of outer covering 560 may be joined to inner covering 532 of outer frame assembly 510, and the lower, ventricle end of leaflets 570 may form free edges 575, though coupled to the lower ends of commissure posts 552.

Although inner valve assembly 540 is shown as having three leaflets, in other embodiments, an inner valve assembly can include any suitable number of leaflets. The leaflets 570 are movable between an open configuration and a close configuration in which the leaflets 570 coapt, or meet in a sealing abutment.

At the lower, or ventricle end, leaflets 570 may have a smaller perimeter than outer covering 560. Thus, the free lower edges of the leaflets, between commissure posts 552 (each portion of leaflets 570 between adjacent commissure posts being referred to as a "belly" of leaflets 570) are spaced radially from the lower edge of outer covering 560 of the inner valve assembly 540. This radial spacing facilitates movement of the leaflets 570 from the open position to the closed position as the counterflow of blood from the ventricle to the atrium during systole can catch the free edges of the bellies and push the leaflets 570 closed (e.g., coapt).

Outer covering 530 of the outer frame assembly 510 and inner covering 532 of outer frame assembly 510, outer covering 560 of the inner valve assembly 540 and leaflets 570 of the inner valve assembly 540 may be formed of any suitable material, or combination of materials, such as those discussed above. In this embodiment, the inner covering 532 of the outer frame assembly 510, the outer covering 560 of the inner valve assembly 540, and the leaflets 570 of the inner valve assembly 540 are formed, at least in part, of porcine pericardium. Moreover, in this embodiment, the outer covering 530 of the outer frame assembly 510 is formed, at least in part, of polyester.

In another embodiment, valve leaflets 570 may optionally have a surface that has been treated with (or reacted with) an anti-coagulant, such as, without limitation, immobilized heparin. Such currently available heparinized polymers are known and available to a person of ordinary skill in the art.

Inner valve assembly 540 is be substantially cylindrical, and outer frame assembly 510 is be tapered, extending from a smaller diameter (slightly larger than the outer diameter of inner valve assembly 540) at a lower, ventricle portion 512 (where it is coupled to inner valve assembly 540) to a larger diameter, atrium portion 516, with an intermediate diameter, annulus portion 514 between the atrium and ventricle portions.

As shown, a tapered annular space or pocket 585 is thus formed between the outer surface of inner valve assembly 540 and the inner surface of outer frame assembly 510, open to the atrium end of valve assembly 500. As shown, pocket closure 580 is coupled along the periphery of the upper end of the inner valve assembly 540. In some embodiments, the pocket closure 580, or a portion thereof, can be coupled along any suitable portion of the inner valve assembly 540.

As discussed above, pocket closure 580 can be formed at least in part of any suitable material that is sufficiently porous to allow blood, including particularly red blood cells, to enter pocket 585, but is not so porous as to allow undesirably large thrombi to leave the pocket 585, or to allow washout of thrombus formed in the pocket 585. In this embodiment, pocket closure 580 is formed entirely of knit polyester (i.e., PET warp knit fabric) having apertures of about 90-120 microns. In some embodiments, a pocket closure can include apertures less than about 160 microns.

Figure 10:
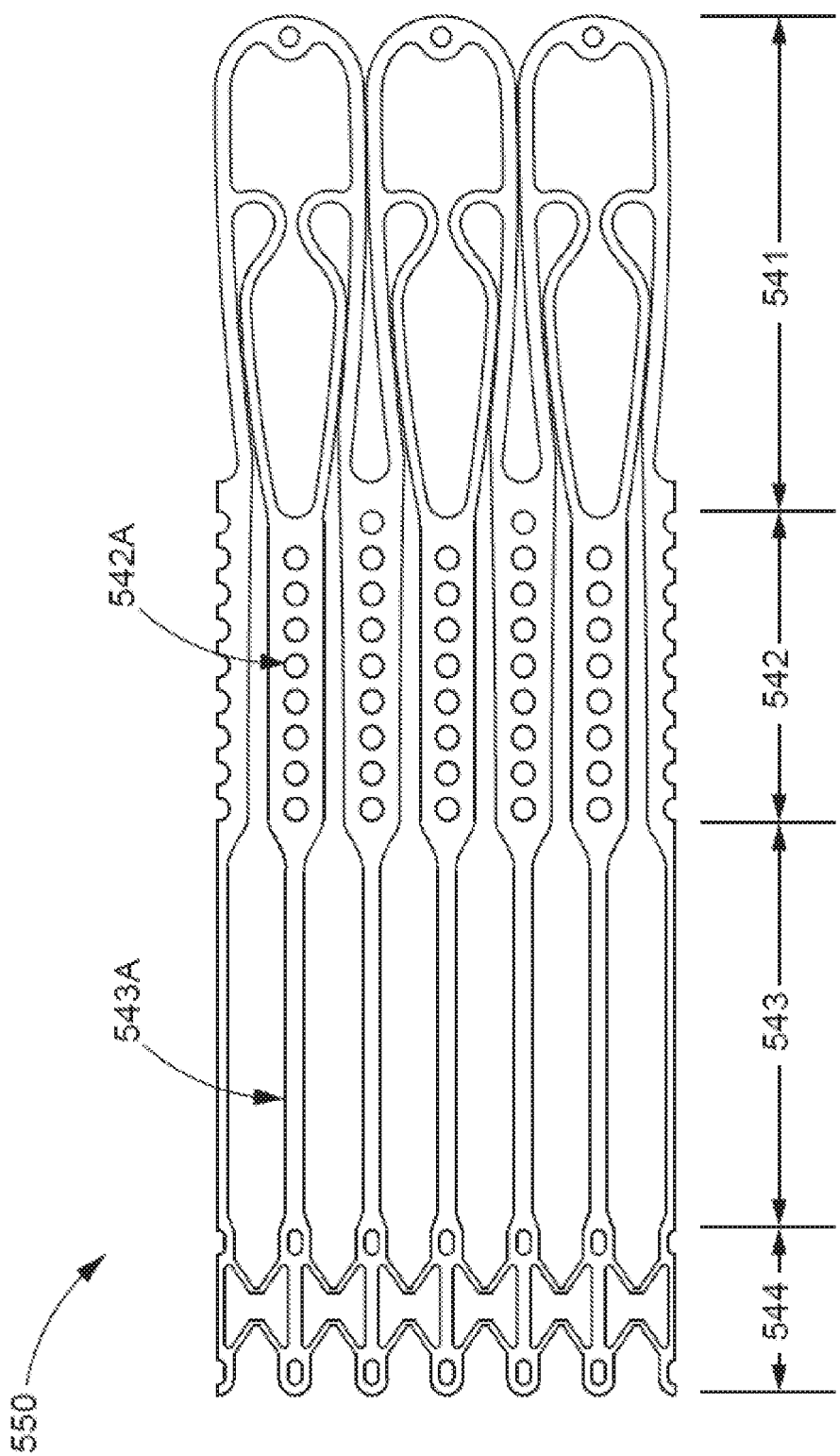
FIG. 10 is an opened and flattened view of the inner frame of the valve of FIGS. 7-9, in an unexpanded configuration.
Figure 11:
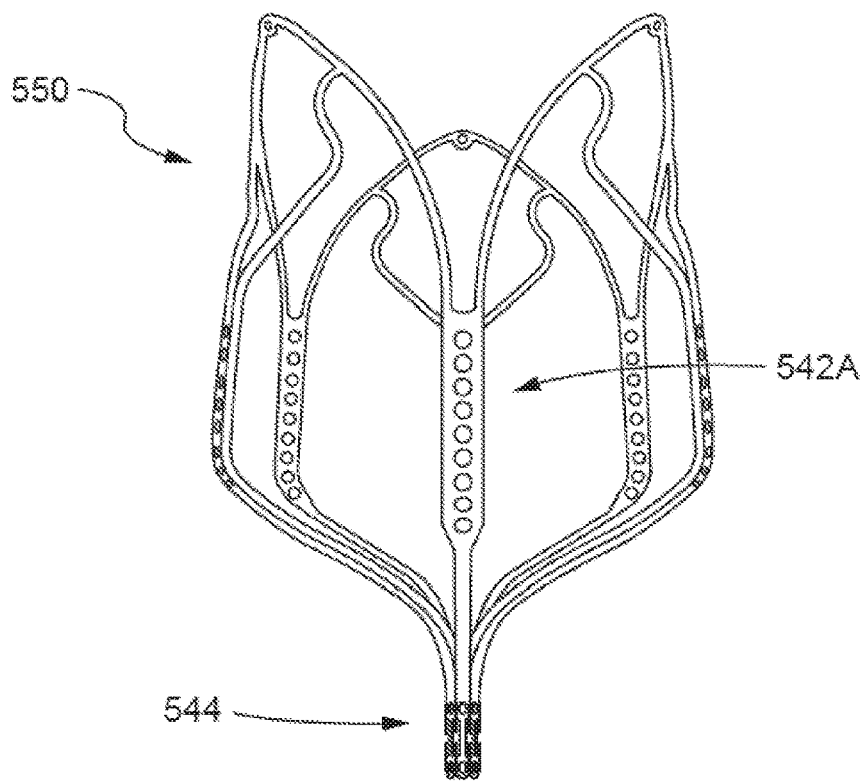
FIGS. 11 and 12 are side and bottom views, respectively, of the inner frame of FIG. 10 in an expanded configuration.
Figure 12:
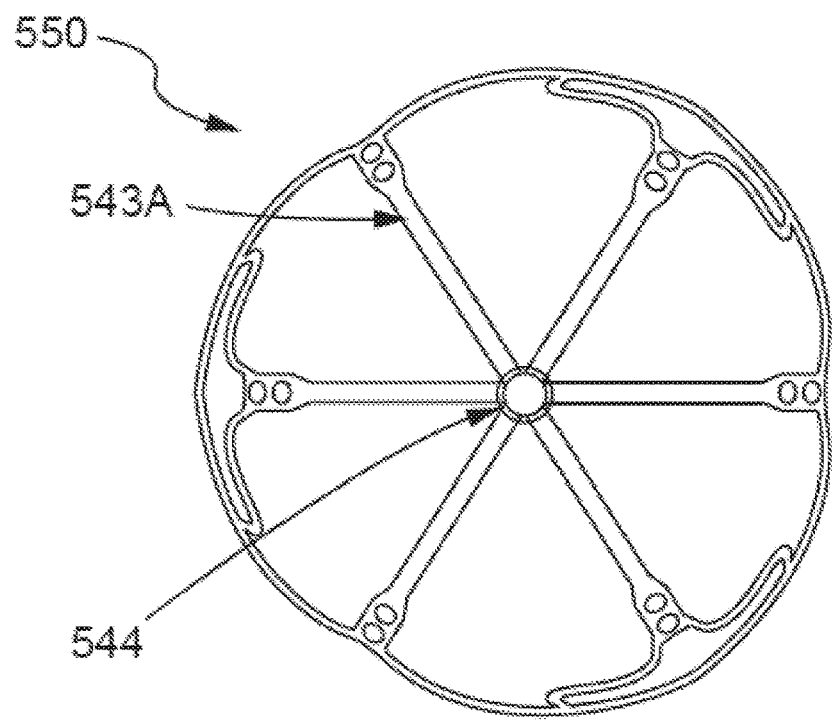

Inner frame 550 is shown in more detail in FIGS. 10-12. Specifically, FIGS. 10-12 show inner frame 550 in an undeformed, initial state (FIG. 10), a side view of the inner frame 550 in a deployed configuration (FIG. 11), and a bottom view of the inner frame 550 in a deployed configuration (FIG. 12), respectively, according to an embodiment.

In this embodiment, inner frame 550 is formed from a laser-cut tube of Nitinol®. Inner frame 550 is illustrated in FIG. 10 in an undeformed, initial state, i.e. as laser-cut, but cut and unrolled into a flat sheet for ease of illustration. Inner frame 550 can be divided into four portions, corresponding to functionally different portions of the inner frame 550 in final form: atrial portion 541, body portion 542, strut portion 543, and tether clamp portion 544. Strut portion 543 includes six struts, such as strut 543A, which connect body portion 542 to tether clamp portion 544.

Connecting portion 544 includes longitudinal extensions of the struts, connected circumferentially by pairs of opposed, slightly V-shaped connecting members (or "micro-Vs"). Connecting portion 544 is configured to be radially collapsed by application of a compressive force, which causes the micro-Vs to become more deeply V-shaped, with the vertices moving closer together longitudinally and the open ends of the V shapes moving closer together circumferentially. Thus, connecting portion 544 can be configured to compressively clamp or grip one end of a tether, either connecting directly onto a tether line (e.g. braided filament line) or onto an intermediate structure, such as a polymer or metal piece that is in term firmly fixed to the tether line.

In contrast to connecting portion 544, atrial portion 541 and body portion 542 are configured to be expanded radially. Strut portion 543 forms a longitudinal connection, and radial transition, between the expanded body portion and the compressed connecting portion 544.

Body portion 542 includes six longitudinal posts, such as post 542A. The posts can be used to attach leaflets 570 to inner frame 540, and/or can be used to attach inner assembly 540 to outer assembly 510, such as by connecting inner frame 550 to outer frame 520. In the illustrated embodiment, the posts include openings through which connecting members (such as suture filaments and/or wires) can be passed to couple the posts to other structures.

Inner frame 550 is shown in a fully deformed, i.e. to the final, deployed configuration, in side view and bottom view in FIGS. 11 and 12, respectively.

Figure 13:
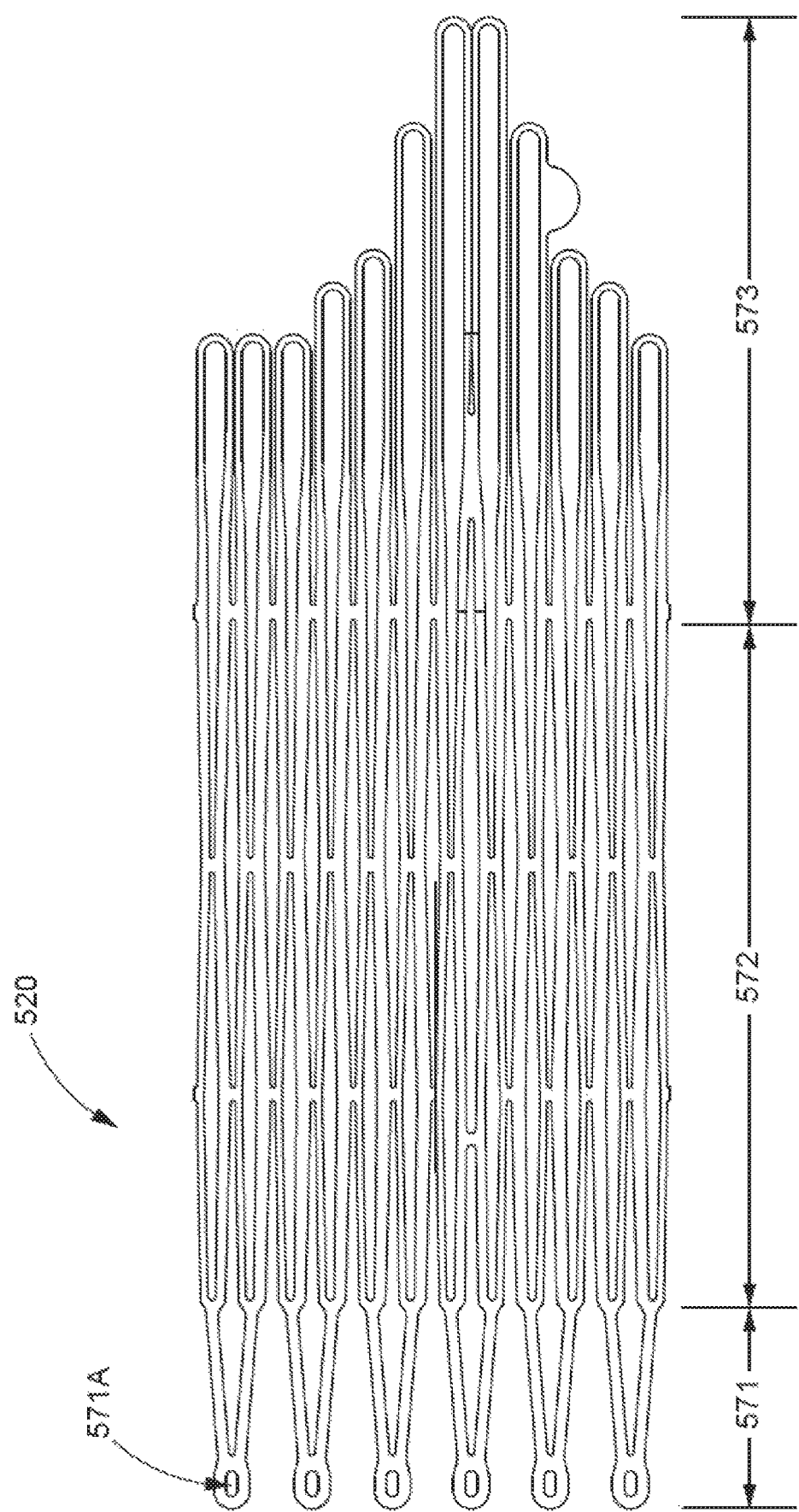
FIG. 13 is an opened and flattened view of the outer frame of the valve of FIGS. 7-9, in an unexpanded configuration.
Figure 14:
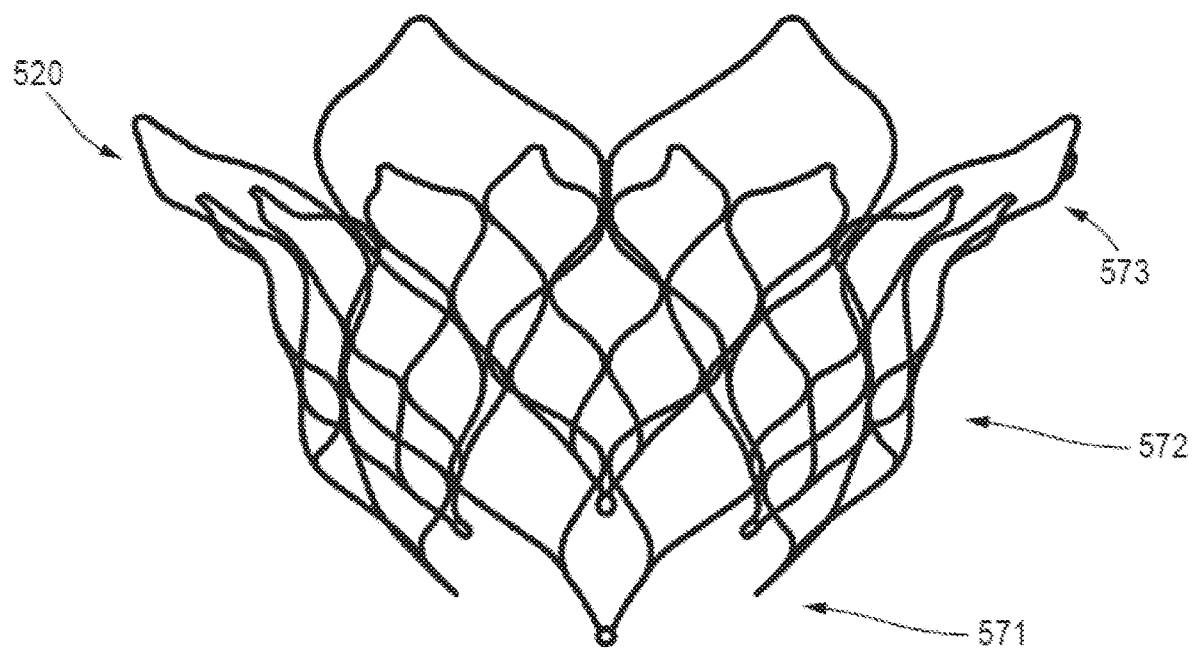
FIGS. 14 and 15 are side and top views, respectively, of the outer frame of FIG. 13 in an expanded configuration.
Figure 15:
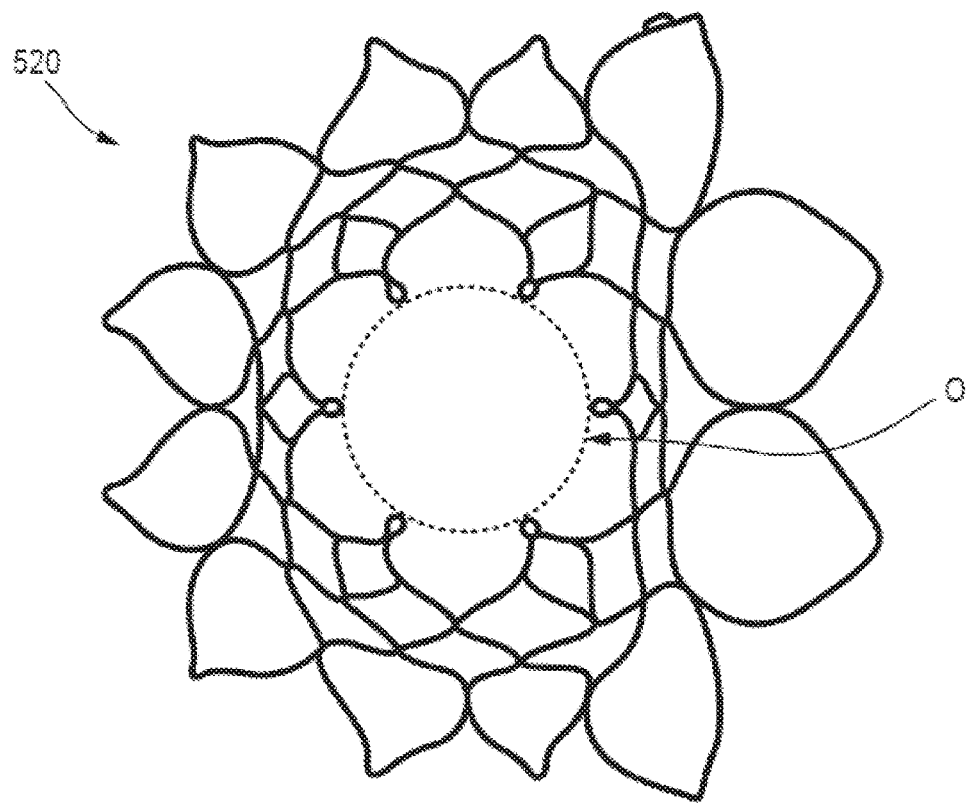

Outer frame 520 of valve 500 is shown in more detail in FIGS. 13-15. In this embodiment, outer frame 520 is also formed from a laser-cut tube of Nitinol®. Outer frame 520 is illustrated in FIG. 13 in an undeformed, initial state, i.e. as laser-cut, but cut and unrolled into a flat sheet for ease of illustration. Outer frame 520 can be divided into a coupling portion 571, a body portion 572, and a cuff portion 573, as shown in FIG. 13.

Coupling portion 571 includes multiple openings or apertures, such as 571A, by which outer frame 520 can be coupled to inner frame 550, as discussed in more detail below.

Outer frame 520 is shown in a fully deformed, i.e. to the final, deployed configuration, in side view and top view in FIGS. 14 and 15, respectively. As best seen in FIG. 15, the lower end of coupling portion 571 forms a roughly circular opening (identified by "O" in FIG. 15). The diameter of this opening preferably corresponds approximately to the diameter of body portion 542 of inner frame 550, to facilitate coupling of the two components of valve 500.

Figure 16:
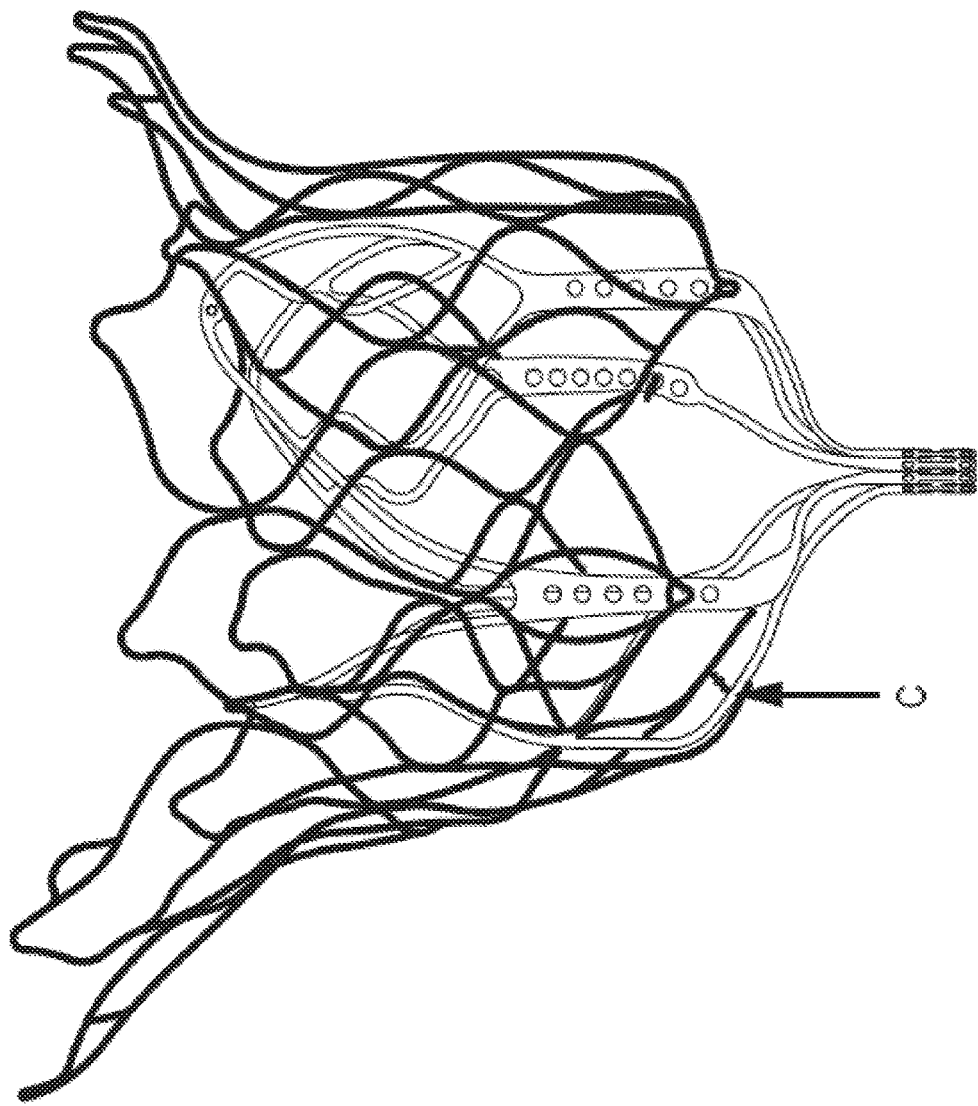
FIGS. 16-18 are side, front, and top views of an assembly of the inner frame of FIGS. 10-12 and the outer frame of FIGS. 13-15.
Figure 17:
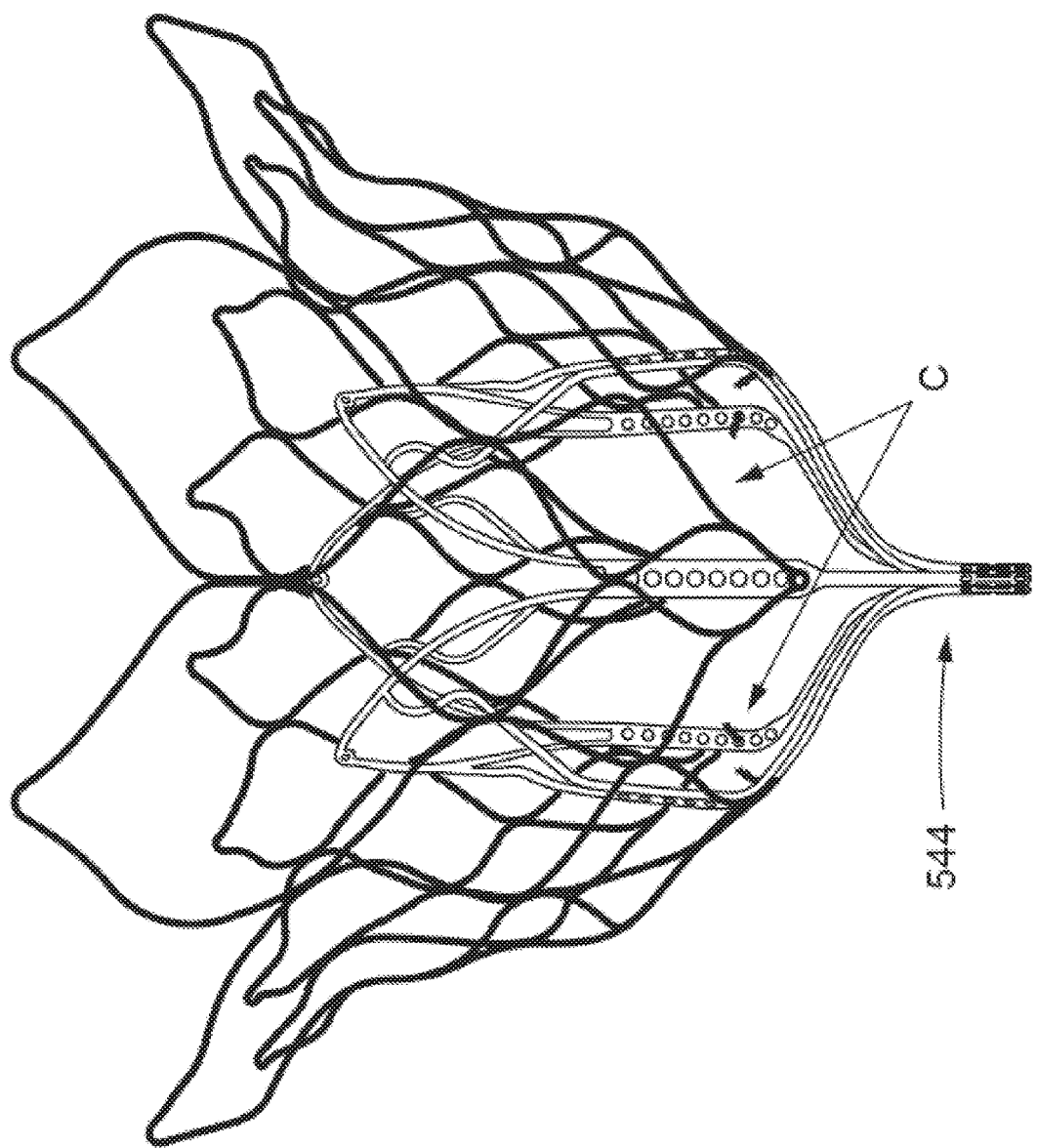
Figure 18:
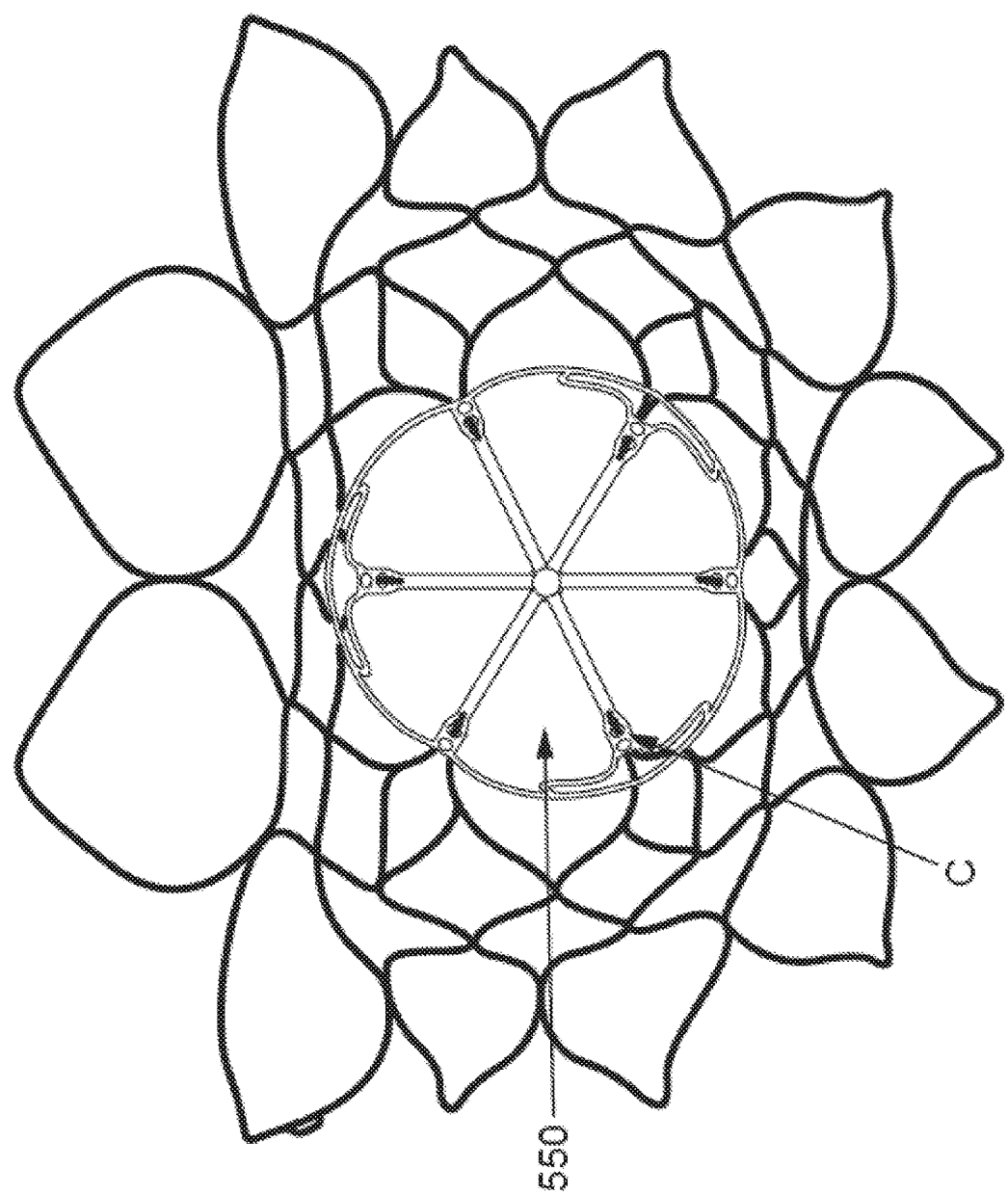

Outer frame 520 and inner frame 550 are shown coupled together in FIGS. 16-18, in front, side, and top views, respectively. The two frames collectively form a structural support for a prosthetic valve such as valve 500. The frames support the valve leaflet structure (e.g., leaflets 570) in the desired relationship to the native valve annulus, support the coverings (e.g., outer covering 530, inner covering 532, outer covering 560) for the two frames to provide a barrier to blood leakage between the atrium and ventricle, and couple to the tether (e.g., tether assembly 590) (by the inner frame 550) to aid in holding the prosthetic valve in place in the native valve annulus by the tether connection to the ventricle wall. The outer frame 520 and the inner frame 550 are connected at six coupling points (representative points are identified as "C"). In this embodiment, the coupling points are implemented with a mechanical fastener, such as a short length of wire, passed through aperture (such as aperture 571A) in coupling portion 571 of outer frame 520 and corresponding openings in longitudinal posts (such as post 542A) in body portion 542 of inner frame 550. Inner frame 550 is thus disposed within the outer frame 520 and securely coupled to it.

Figure 19:
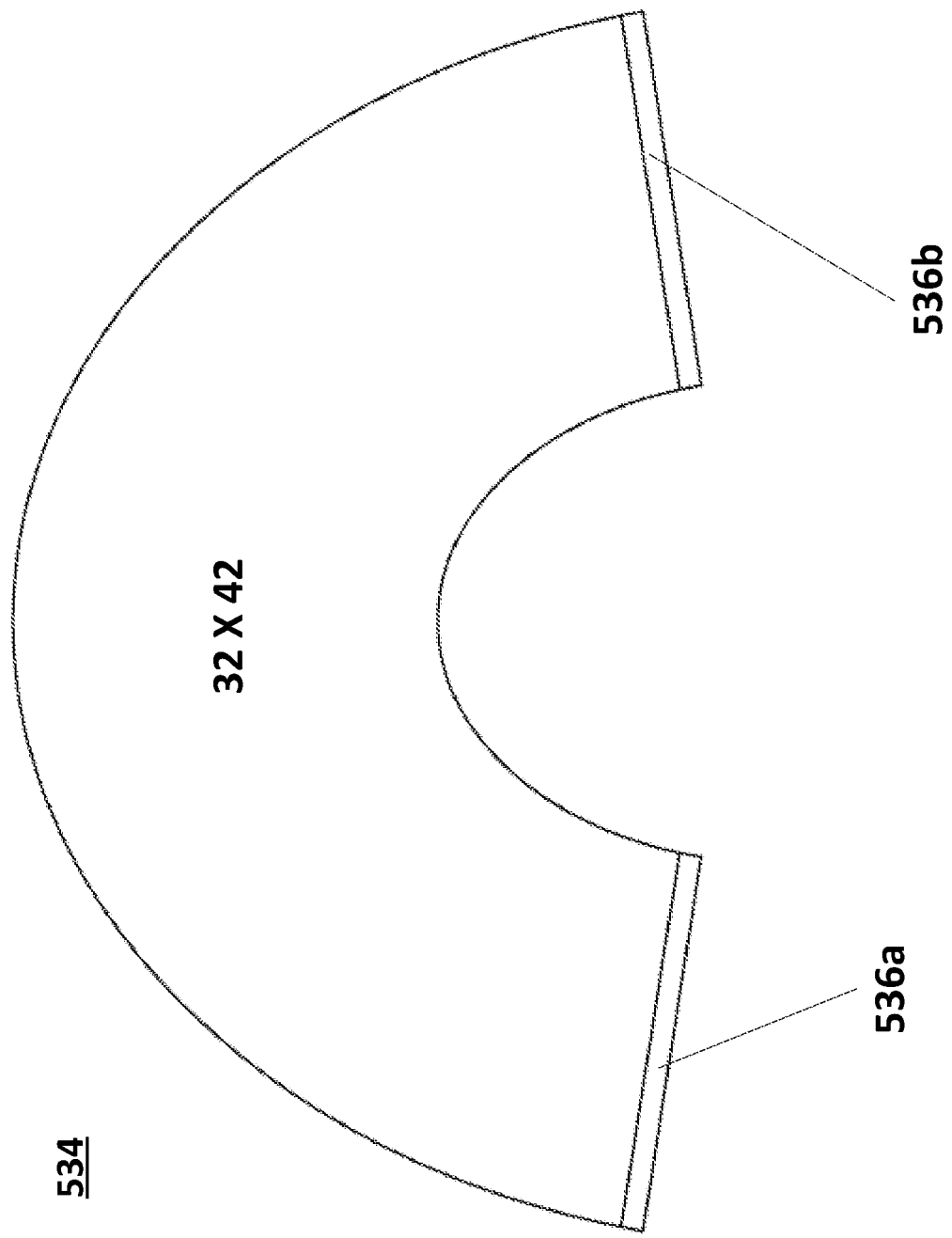
FIG. 19 is a plan view of a fabric pattern for the inner and outer coverings of the outer frame assembly of the valve of FIGS. 7-9.

A template 534 (or design pattern) for cutting, shaping, and sizing outer covering 530 of outer frame assembly 510 and/or inner covering 532 of outer frame assembly is illustrated in FIG. 19, according to an embodiment. Design pattern 534 includes attachment location indications 536a, 536b. To arrange outer covering 530 into an assembled configuration (i.e., either coupled to or ready to be coupled to outer frame 520), the two ends of the outer covering 530 are coupled together (e.g., sewn) in accordance with the attachment location indications 536a, 536b of the template 534. Similarly, inner covering 532 is arranged into an assembled configuration by coupling (e.g., sewing) its ends together in accordance with the attachment location indications 536a, 536b.

Figure 20:
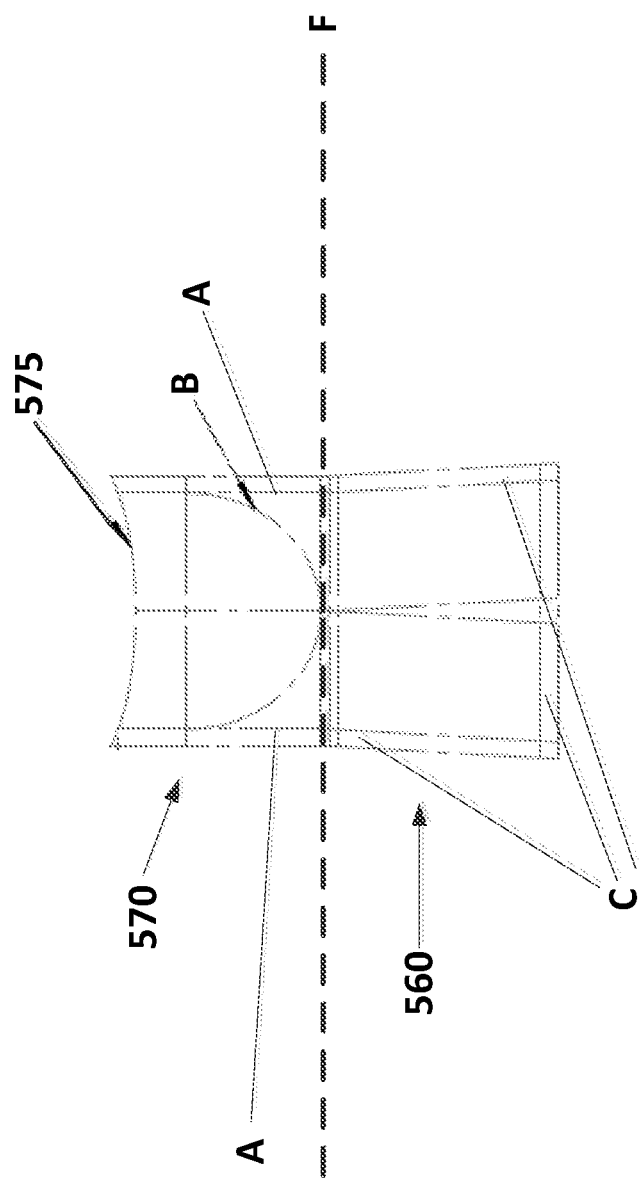
FIG. 20 is a plan view of a fabric pattern for the leaflets and outer covering of the inner valve assembly of the valve of FIGS. 7-9.

FIG. 20 illustrates a design pattern of one leaflet 570 and associated portion of outer covering 560 of the inner valve assembly in its initial, pre-assembled state (i.e., not attached to inner frame 550), according to an embodiment. As discussed above, the portion of leaflet 570 between adjacent commissure posts is referred to as a "belly" of the leaflet 570. The belly has a curved edge indicated with reference 'B' in FIG. 20. During assembly of inner valve assembly 540, the leaflet 570 is coupled to the inner frame 550 of the inner valve assembly 540. Specifically, the belly edge B of the leaflet 570, or a portion thereof, is coupled to the inner frame 550 at the arch portion of the inner frame 550. In addition, outer covering 560 is folded over a portion of the inner frame 550 (e.g., the arch portion) along the axis indicated with 'F', and coupled to a portion of the inner frame 550 (e.g., the commissure post 552) along attachment line A. As shown, a coupling area C (e.g., a stitching area), is disposed outside and adjacent to attachment line A. Coupling area C can facilitate the assembly process. Subsequently, excess leaflet material and/or excess outer covering material can be cut away and disposed of or reused. For example, material disposed between the belly edge B and the F-axis, or material in the coupling area C, may, in some embodiments, be unnecessary material and thus can be cut away from the leaflet 570 and/or outer covering 560. The assembly process can be repeated for each leaflet 570, each outer covering 560, and each commissure post 552.

The leaflets 570 and the outer covering 560 can have any suitable size, shape, material, and/or configuration. For example, in this embodiment, leaflets 570 and/or outer covering 560 is formed of fixed porcine pericardium, with a thickness of about 0.01 inches.

Figure 21:
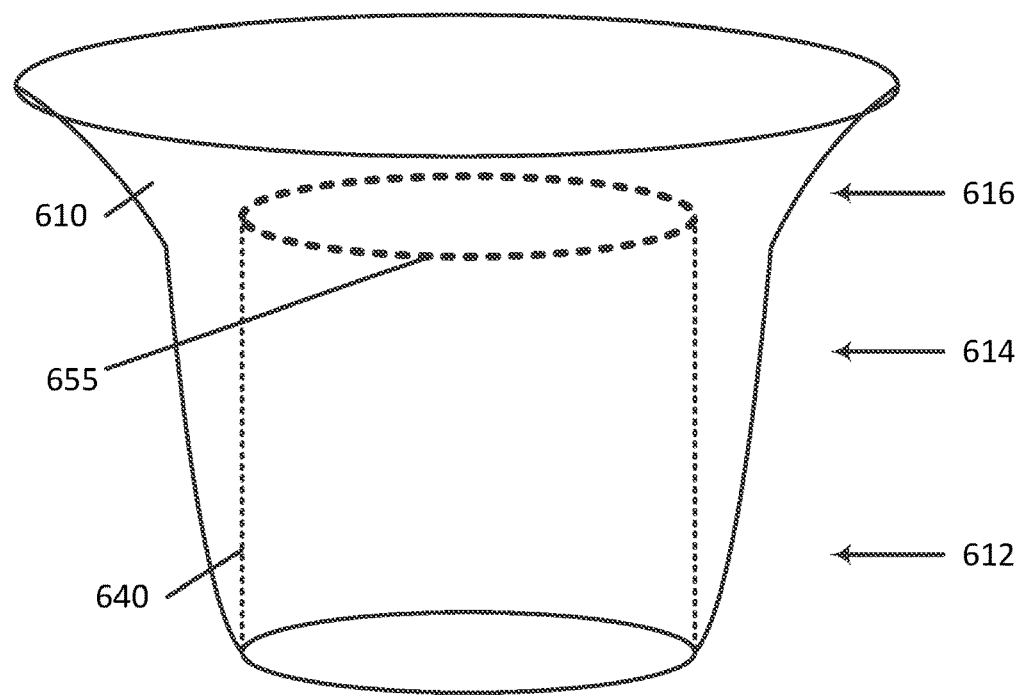
FIGS. 21 and 22 are schematic perspective and side cross sectional views of a prosthetic heart valve according to another embodiment.
Figure 22:
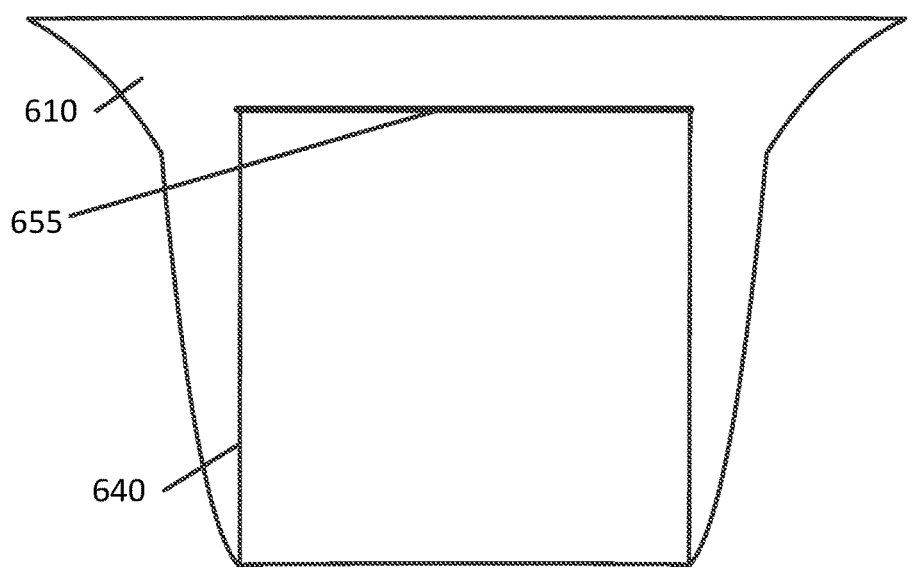

A schematic representation of another embodiment of a prosthetic heart valve is shown in FIGS. 21 and 22. Prosthetic heart valve 600 is designed to replace a damaged or diseased native heart valve such as a mitral valve. Valve 600 includes an outer frame assembly 610 and an inner valve assembly 640 coupled to the outer frame assembly 610.

Although not separately shown in the schematic illustration of outer frame assembly 610 in FIGS. 21 and 22, outer fame assembly 610 may be formed of an outer frame 620, covered on all or a portion of its outer face with an outer covering 630, and covered on all or a portion of its inner face by an inner covering 632. The materials and construction of the components of prosthetic heart valve 600 can be similar to those of the other embodiments described above. The following discussion focuses on the aspects of this embodiment that differ from the previous embodiments.

Inner valve assembly 640 includes an inner frame 650 (not shown), an outer covering 660 (not shown), leaflets 670 (not shown), and atrial structure 655 (e.g., halo). As shown, the halo 655 is disposed at the atrium portion 616 of inner valve assembly 640. In such a configuration, when valve 600 is implanted into a heart of a patient, halo 655 will be disposed above the atrial floor and/or native valve annulus of the patient's heart. In this manner, the halo 655 provides extended functionality (e.g., above the native mitral valve annulus) of the inner frame 650. In some instances, for example, if prosthetic leaflets are seated too low relative to the native valve annulus, the leaflets may improperly coapt (e.g., incomplete coaptation) and/or hemodynamic leakage can occur. Thus, disposing halo 655 above the native valve annulus can provide for and/or promote complete coaptation.

Halo 655 can be formed from any suitable method and material. For example, in some embodiments, halo 655 can be formed from a substantially circular piece of wire. In such embodiments, halo 655 can be coupled to (e.g., sewn) to inner frame 650.

Outer covering 630 and inner covering 632 of outer frame 620, outer covering 660 and leaflets 670 may be formed of any suitable material, or combination of materials, such as those discussed above in connection with other embodiments.

As shown in FIGS. 21 and 22, inner valve assembly 640 may be substantially cylindrical, and outer frame assembly 610 may be tapered, extending from a smaller diameter (slightly larger than the outer diameter of inner valve assembly 640) at a lower, ventricle portion 612 (where it is coupled to inner valve assembly 640) to a larger diameter, atrium portion 616, with an intermediate diameter, annulus portion 614 between the atrium and ventricle portions.

In some embodiments, the outer surface of inner valve assembly 610, and/or the inner surface of outer frame assembly 640, need not by circular in cross-section as shown schematically in FIGS. 21 and 22, but may be of non-constant radius at a given location along the central axis of valve 600.

The atrial halo 655 functions by extending the inner frame of an inner valve assembly above the plane of atrial floor in an improved prosthetic heart valve that includes an inner frame that holds the leaflets and which is disposed within an outer frame for reducing or preventing leaking when the prosthetic heart valve is disposed within a heart valve (e.g., mitral valve, tricuspid valve).

A benefit to having leaflets within a raised leaflet silo or cylinder (e.g., halo 650) is improved blood flow and leaflet closure. It has been observed that where the leaflet cylinder is at the atrial floor, leaflet coaptation is incomplete and can result in hemodynamic leakage.

Accordingly, by providing an atrial halo or ring structure that is raised above the plane of the native annulus or atrial floor, complete leaflet coaptation is encouraged. During ventricular contraction or systole, the blood is ejected towards aortic valve to exit the heart but is also ejected towards the prosthetic mitral valve, which needs to remain closed during systole. Retrograde blood hitting the prosthetic valve leaflets cause the leaflets to close, preventing regurgitation into the left atrium. During diastole or ventricular filling, the blood needs to flow from the atrium into the ventricle without obstruction. However, when prosthetic leaflets are not properly placed or properly aligned, the leaflets can obstruct efficient filling of the ventricle or cause uneven ventricular output.

Figure 23:
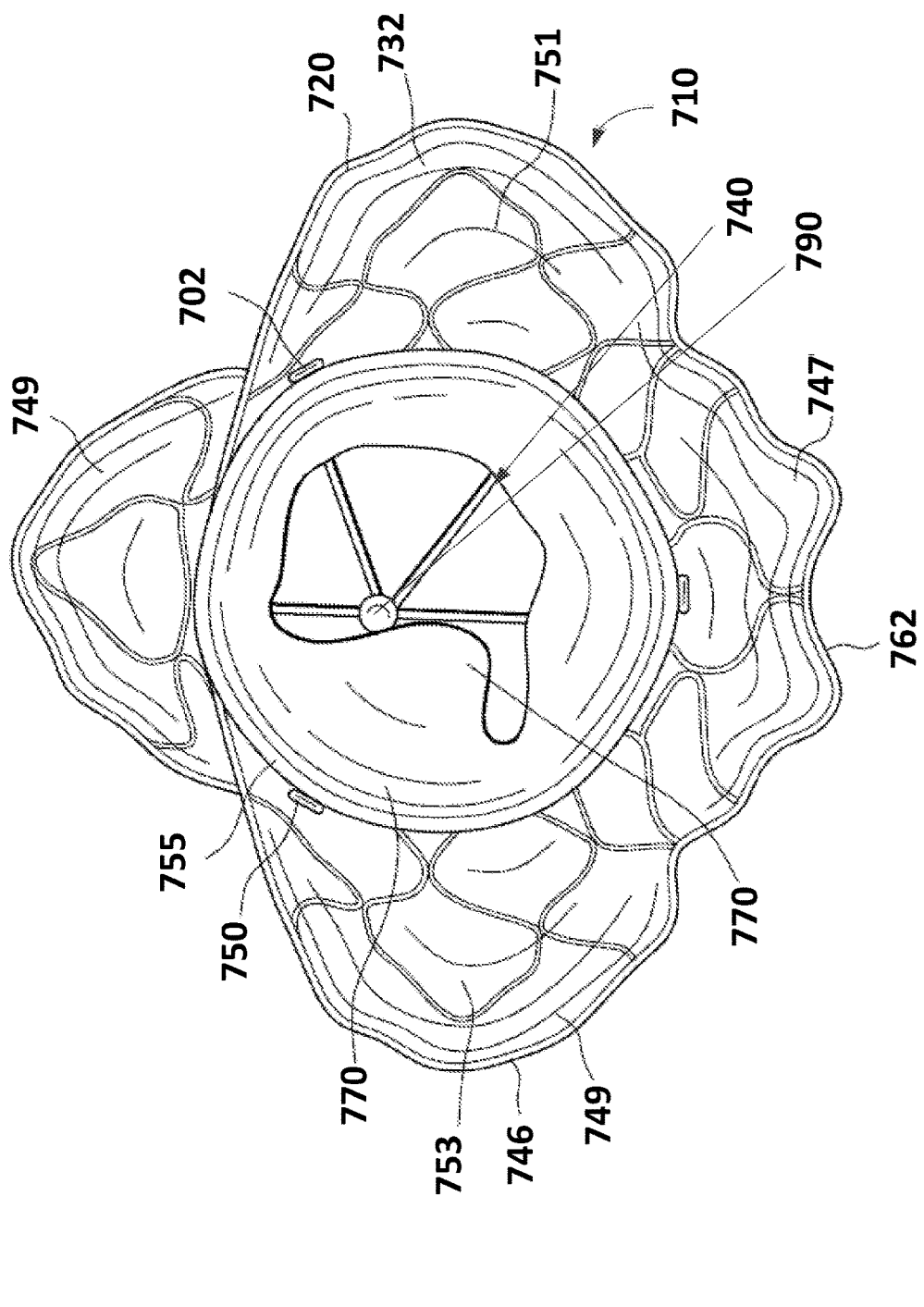
FIGS. 23-25 are top and perspective views of a prosthetic heart valve according to another embodiment.

FIG. 23 is a top-view of a prosthetic heart valve 700 according to an embodiment that is one possible implementation of the prosthetic heart valve shown schematically in FIGS. 21 and 22. Prosthetic heart valve 700 includes an outer frame assembly 710, an inner valve assembly 740, and a tether assembly 790. The inner valve assembly 740 includes an inner frame 750, and outer covering 760 (not shown), leaflets 770, and atrial structure 755 (e.g., halo). Halo 755 can be formed from a circular piece of wire that can be connected to the inner frame 750 and sewn to the leaflets 770. The inner frame 750 can be made of Nitinol® wire that supports leaflets 770 sewn to the inner frame 750 and functions as a valve. The inner frame 750 shown in FIG. 23 includes three U-shaped wire components joined at their opened ends to form junctions 702. Leaflets 770 are sewn to these components to form articulating leaflets, creating and functioning as a prosthetic valve (e.g., prosthetic mitral valve, prosthetic tricuspid valve).

In some embodiments, the inner frame 750 has tether attachment apertures 711 (not shown) for attaching tether assembly 790. Tether assembly 790 is connected to epicardial securing pad 754 (not shown).

In operation, the inner frame 750 (with leaflets 770), is disposed within and secured within the outer frame 720 of the outer frame assembly 710. Outer frame 720 includes an outer covering 730 (not shown) (e.g., tissue material) and an inner covering 732 (e.g., tissue material). Outer frame 720 has an articulating collar 746 which has a collar cover 748. Articulating collar 746 is configured (e.g., shaped and sized) to solve leakage issues arising from native structures. In particular, collar 746 is composed of an A2 segment 747, a P2 segment 749, and two commissural segments, the A1-P1 segment 751, and the A3-P3 segment 753. The collar 746 may also have, in some embodiments a shortened or flattened or D-shaped section 762 of the A2 segment in order to accommodate and solve left ventricular outflow tract (LVOT) obstruction issues.

In operation, the valve 700 may be deployed as a prosthetic mitral valve using catheter delivery techniques. The entire valve 700 is compressed within a narrow catheter and delivered to the annular region of the native valve, preferably the left atrium, with a pre-attached tether apparatus. Upon delivery, the valve 700 is pushed out of the catheter where it springs open into its pre-formed functional shape without the need for manual expansion (e.g., manual expansion using an inner balloon catheter). When the valve 700 is pushed and/or pulled into place, the outer frame assembly 710 is seated in the native valve annulus (e.g., native mitral annulus), leaving the articulating collar 746 to engage the atrial floor and prevent pull-through (where the valve is pulled into the ventricle). In such embodiments, it is not necessary to cut-away the native leaflets, as has been taught in prior prosthetic efforts. Instead, the native leaflets can be used to provide a tensioning and/or sealing function around the outer frame assembly 710. It is advantageous for the valve 700 to be asymmetrically deployed in order to address LVOT problems where non-accommodating prosthetic valves push against the A2 anterior segment of the valve (e.g., mitral valve) and close blood flow through the aorta, which anatomically sits immediately behind the A2 segment of the mitral annulus. Thus, D-shaped section 762 is deployed substantially immediately adjacent/contacting the A2 segment since the flattened D-shaped section 762 is structurally smaller and has a more vertical profile (closer to paralleling the longitudinal axis of the outer stent) and thereby provides less pressure on the A2 segment. Once the valve 700 is properly seated, tether assembly 790 may be extended out through the apical region of the left ventricle and secured using an epicardial pad 754 or similar suture-locking attachment mechanism (not shown).

In an alternate embodiment, the tether assembly 790 is on the outer frame 720, which would then have tether attachment apertures 713 for attaching tether assembly 790 to epicardial securing pad 754.

Figure 24:
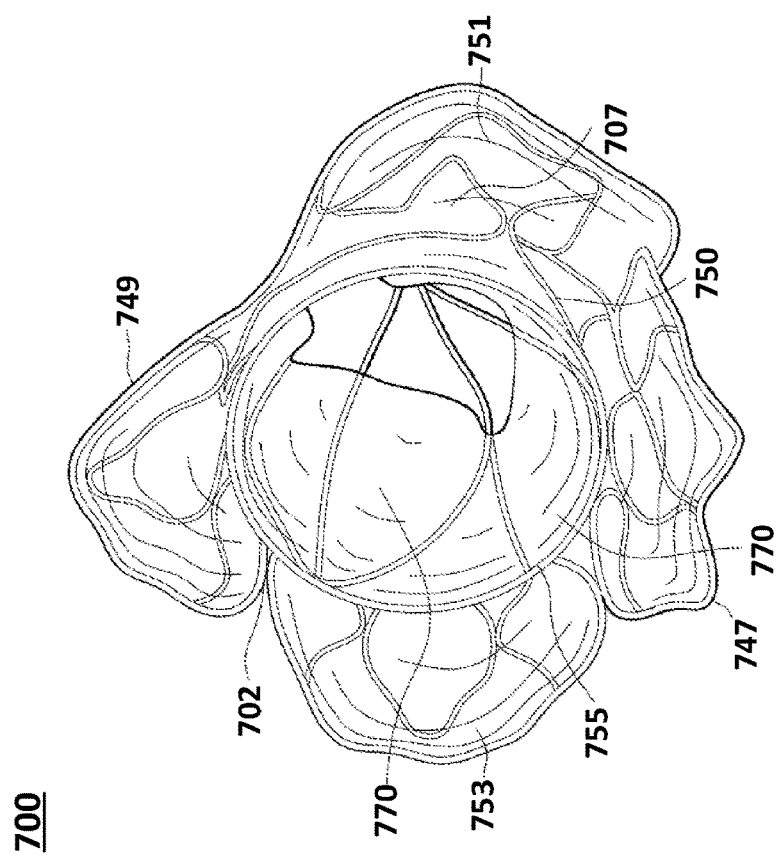
Figure 26:
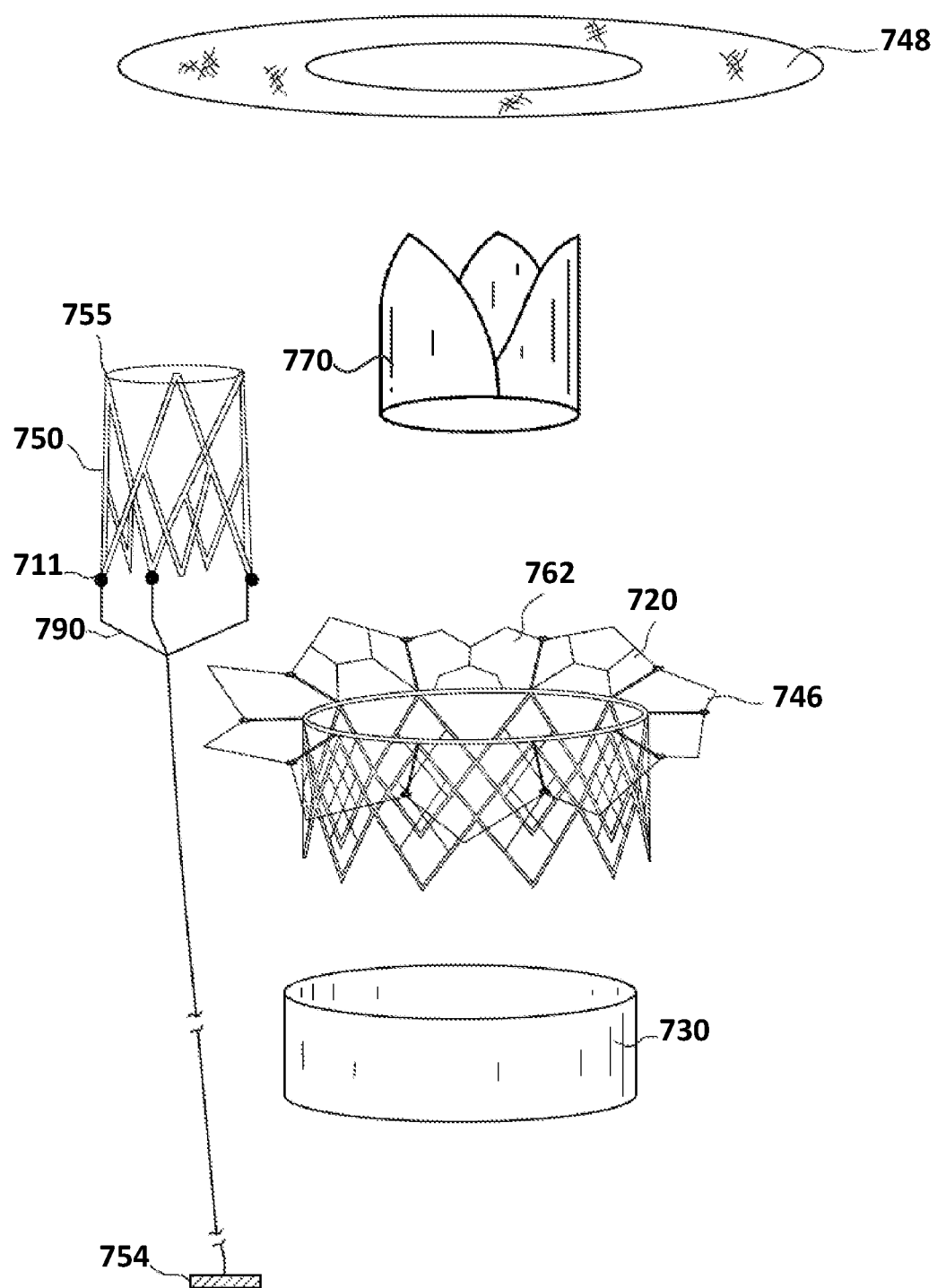
FIG. 26 is an exploded view of a prosthetic heart valve system according to another embodiment.

FIG. 24 is a perspective view of the A1-P1 side of the prosthetic heart valve 700 according to an embodiment. FIG. 24 shows one of the three U-shaped wire components of inner frame 750 joined at their opened ends to form junctions 702. Although three U-shaped wire components are shown, in other embodiments, any suitable number of U-shaped wire components can be joined at their opened ends to form junctions. Similarly, in some embodiments, the wire components of inner frame 750 can by any suitable shape or size. Leaflets 770 are sewn to these components to form articulating leaflets 770 creating and functioning as a prosthetic heart valve (e.g., mitral valve, tricuspid valve). Atrial halo 755 is shown with the plane of the circular wire above the plane of the majority of collar except for the vertical A2 segment 747, the P2 segment 749, and the commissural A1-P1 segment 751 an A3-P3 segment 753. FIG. 26 shows how upon deployment blood would fill the void or gap 707 between the inner frame 750 and the outer frame 720 at the A1-P1 segment 751 of the valve 700. This blood creates a temporary fluid seal that would pool in that space and provide a pressure buffer against the leakage inducing forces that accompany systolic and diastolic related intra-atrial and intra-ventricular pressure.

Figure 25:
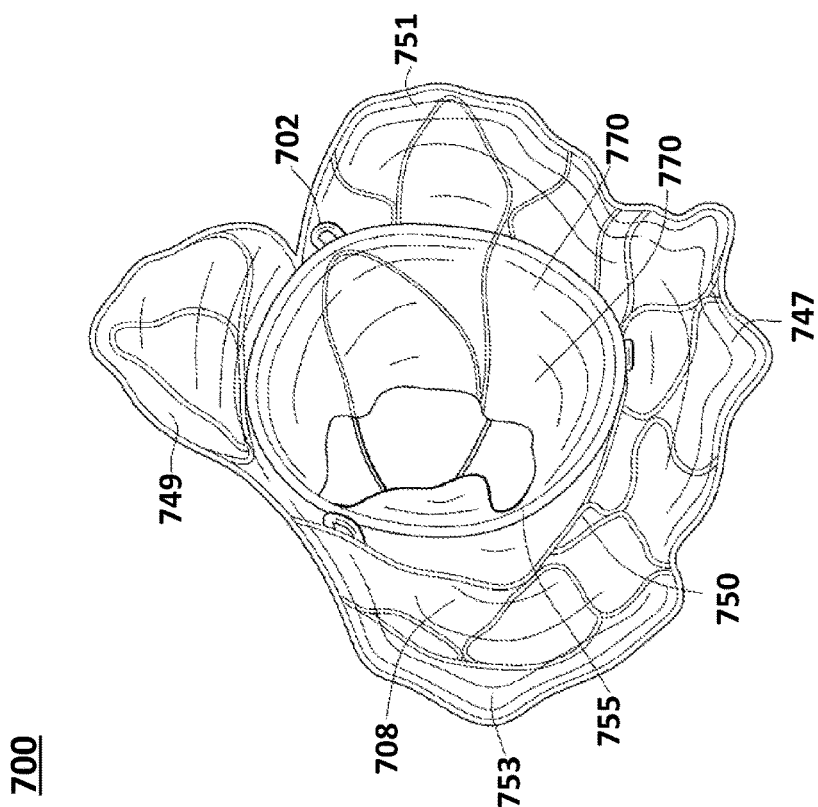

FIG. 25 is a perspective view of the A3-P3 side 753 of prosthetic heart valve 700 according to an embodiment. FIG. 25 shows one of the three U-shaped wire components of inner frame 750 joined at their opened ends to form junctions 702. Leaflets 770 are sewn to these components to form articulating leaflets 770 creating and functioning as a prosthetic tricuspid valve. Atrial halo 755 is shown with the plane of the circular wire above the plane of the majority of collar except for the vertical A2 segment 747, the P2 segment 749, and the commissural A1-P1 segment 751 and A3-P3 segment 753. FIG. 25 shows how upon deployment blood would fill the void or gap 708 between the inner frame 750 and outer frame 720 at the A3-P3 segment 753 area of the valve 700. This blood creates a temporary fluid seal that would pool in that space and provide a pressure buffer against the leakage inducing forces that accompany systolic and diastolic related intra-atrial and intra-ventricular pressure.

FIG. 26 is an exploded view of prosthetic heart valve 700 according to an embodiment. In this valve 700, the inner frame 750 is sewn with tissue 706 and acts a cover to prevent valvular leakage. The inner frame 750 contains the leaflets 770 comprised of articulating leaflets that define a valve function. The leaflets 770 are sewn to the inner frame 750. The inner frame 750 also has tether attachment apertures 711 for attaching tether assembly 790. Tether assembly 790 is shown in this example as connected to epicardial securing pad 754. In operation, the covered inner frame 750 (e.g., covered with outer covering 760) (with leaflets 770), is disposed within and secured within the outer frame 720 of the outer frame assembly 710. Outer frame 720 may also have in various embodiments a covering (e.g., outer covering 730). Outer frame 720 has an articulating collar 746 which has a collar cover 748. Articulating collar 746 may also have in some embodiments a D-shaped section 762 to accommodate and solve left ventricular outflow tract (LVOT) obstruction issues.

In operation, the valve 700 may be deployed as a prosthetic valve (e.g., mitral valve) using catheter delivery techniques. The entire valve 700 is compressed within a narrow catheter and delivered to the annular region of the native valve, such as, for example, with a pre-attached tether assembly 790. There, the valve 700 is pushed out of the catheter where it springs open into its pre-formed functional shape without the need for manual expansion (e.g., manual expansion using an inner balloon catheter). When the valve 700 is pushed and/or pulled into place, the outer frame assembly 710 is seated in the native mitral annulus, leaving the articulating collar 746 to engage the atrial floor and prevent pull-through (where the valve is pulled into the ventricle). In such embodiments, it is not necessary to cut-away the native leaflets, as has been taught in prior prosthetic efforts. Instead, the native leaflets can be used to provide a tensioning and/or sealing function around the outer frame assembly 710. It is advantageous for the valve 700 to be asymmetrically deployed in order to address LVOT problems where non-accommodating prosthetic valves push against the A2 anterior segment of the valve (e.g., the mitral valve) and close blood flow through the aorta, which anatomically sits immediately behind the A2 segment of the mitral annulus. Thus, D-shaped section 762 is deployed immediately adjacent/contacting the A2 segment since the flattened D-shaped section 762 is structurally smaller and has a more vertical profile (closer to paralleling the longitudinal axis of the outer stent) and thereby provides less pressure on the A2 segment. Once the valve 700 is properly seated, tether assembly 790 may be extended out through the apical region of the left ventricle and secured using an epicardial pad 754 or similar suture-locking attachment mechanism.

Any of the prosthetic heart valve embodiments described above can incorporate additional structural features to enhance their performance. The structural features are discussed below with reference to prosthetic heart valve 800, illustrated schematically in perspective and side views in FIGS. 27 and 28, respectively.

As shown, the outer frame 820 has an atrium portion 826, a ventricle portion 822, and an annulus portion 824 disposed between the atrium portion 826 and the ventricle portion 822. The inner frame 850 of the inner valve assembly 840 has a first end and a second end. The inner valve assembly 840 can be coupled to the outer frame 820 by a connection between the first end of the inner frame 850 and the ventricle portion 812 of the outer frame assembly 810. The inner frame assembly 840 can extend from the connection towards the atrium portion 816 of the outer frame assembly 810. The inner frame assembly 840 and the outer frame assembly 810 can diverge from the connection towards the atrium portion 816 of the outer frame assembly 810. The annulus portion 814 of the outer frame assembly 810 can be spaced radially from the inner valve assembly 840 and radially inwardly deflectable towards the inner valve assembly 840 to accommodate a natural heart valve annulus in the annulus portion 814.

The outer frame assembly 810 can be shaped and sized in any suitable manner to facilitate a proper fit into a native heart valve. For example, as shown, the outer frame 820 can be shaped and sized to resemble, at least in part, an hourglass shape. Specifically, the annulus portion 814 of outer frame assembly 810 varies from an intermediate diameter (or perimeter) near ventricle portion 812 to a smaller diameter (or perimeter) near the middle of annulus portion 814, to a larger diameter (or perimeter) near atrium portion 816. Thus, annulus portion 814 has an hourglass shape. Ventricle portion 812 has a maximum diameter larger than a maximum diameter of annulus portion 814. The ventricle portion has a minimum diameter smaller than a minimum diameter of the annulus portion 814.

The diameters and/or perimeters for each portion of the outer frame 820 can be selected based on the size and/or shape of a native heart valve into which prosthetic heart valve 800 is to be implanted. For example, the minimum diameter of the annulus portion 824 of the outer frame 820 can be smaller than that of the native valve annulus. Thus, in such a configuration, the diameters of the ventricle portion 822, annulus portion 824, and atrium portion 826 can collectively promote a suitable fit (e.g., a snug, secure fit) of the prosthetic heart valve 800 in a native heart valve. In this manner, the outer frame 820 can be configured to optimize securement and sealing between the prosthetic heart valve 800 (particularly outer frame assembly 810) and a native valve annulus of a native heart valve. Thus, such a configuration minimizes the likelihood of paravalvular leaks.

Although the outer frame 820 is shown to have a circular cross-section, in some embodiments, the outer frame 820 can by any suitable shape or size. For example, in some embodiments, the outer frame 820 can have a D-shape cross-section. In this manner, the outer frame 820 can have a shape configured to correspond to (e.g., mate with) a native heart valve annulus.

In addition to, or instead of, outer frame 820 and/or outer frame assembly 810 with the hourglass shape described above, valve 800, or in some instances, outer frame 820 and/or outer frame assembly 810, in particular, can be formed to provide stiffness, such as resistance to hoop compression, that is varied spatially, i.e., axially and/or circumferentially.

In this manner, a suitable stiffness profile can be arranged such that the valve 800 promotes a desirable shape and sealing region when disposed in a native heart valve, thus minimizing the likelihood of paravalvular leaks and undesired movement of the valve. Similarly stated, valve 800 can be configured to have a stiffness profile suitable to cause desirable deformation of the native heart valve annulus (i.e., the sealing region), and thus, proper implantation of valve 800.

A desired stiffness profile of prosthetic valve 800 can be achieved by varying properties, characteristics, and/or the arrangement of the outer frame assembly 810 and the inner valve assembly 840. For example, the outer frame 820 and/or the inner frame 850 can contain portions of varying material states. For example, a first portion of outer frame 820 can be in an elastic state, while a second portion of outer frame 820 is in a super-elastic state. Similarly, for example, portions of the outer frame 820 and/or the inner frame 850 can be in an austenitic state and/or a martensitic state (e.g., a stress induced martensitic state). In this manner, portions of valve 800 can be configured to suitably mate with a native valve annulus, thus improving sealing and limiting paravalvular leaks.

In addition, the outer frame assembly 810 and/or inner valve assembly 840 can have varying widths, thicknesses, shapes (e.g., longitudinal shape), angles (e.g., angle of attachment between inner valve assembly 840 and outer frame assembly 810), and the like. In some embodiments, the outer covering 830, inner covering 832, outer covering 860, and/or pocket closure 880 can be configured to determine, at least in part, the stiffness profile and/or shape of valve 800 (e.g., based on sewing pattern).

Figure 29C:
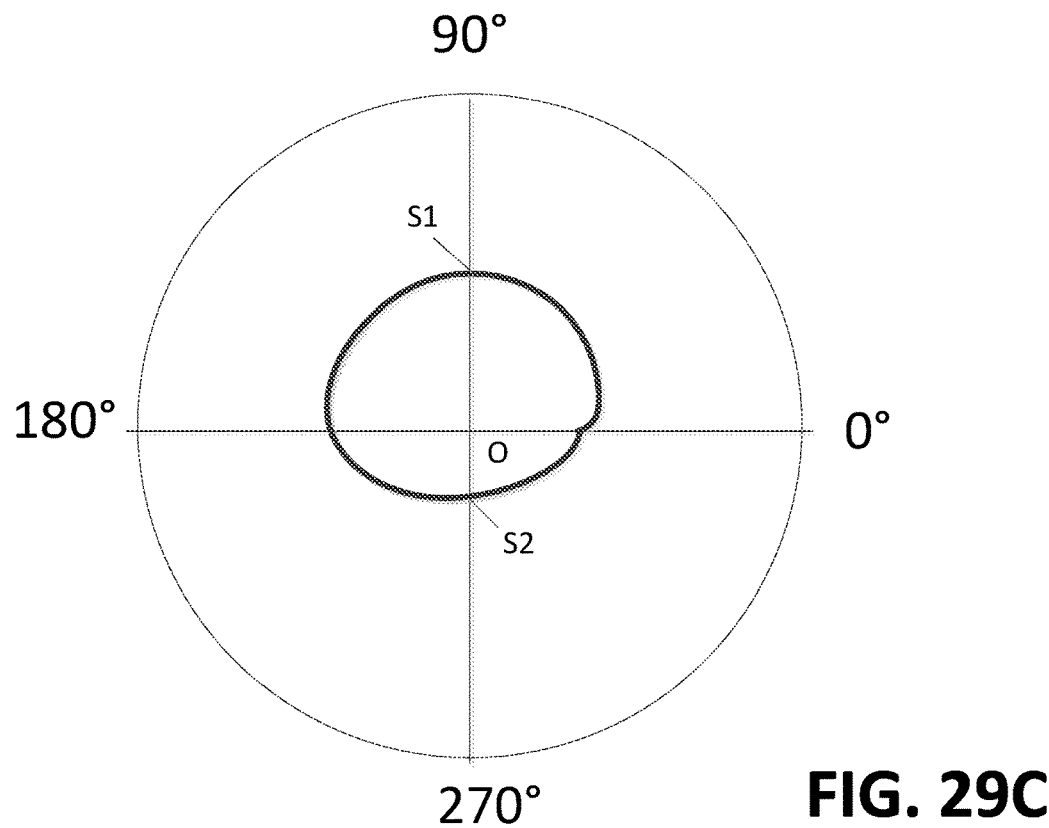
Figure 29D:
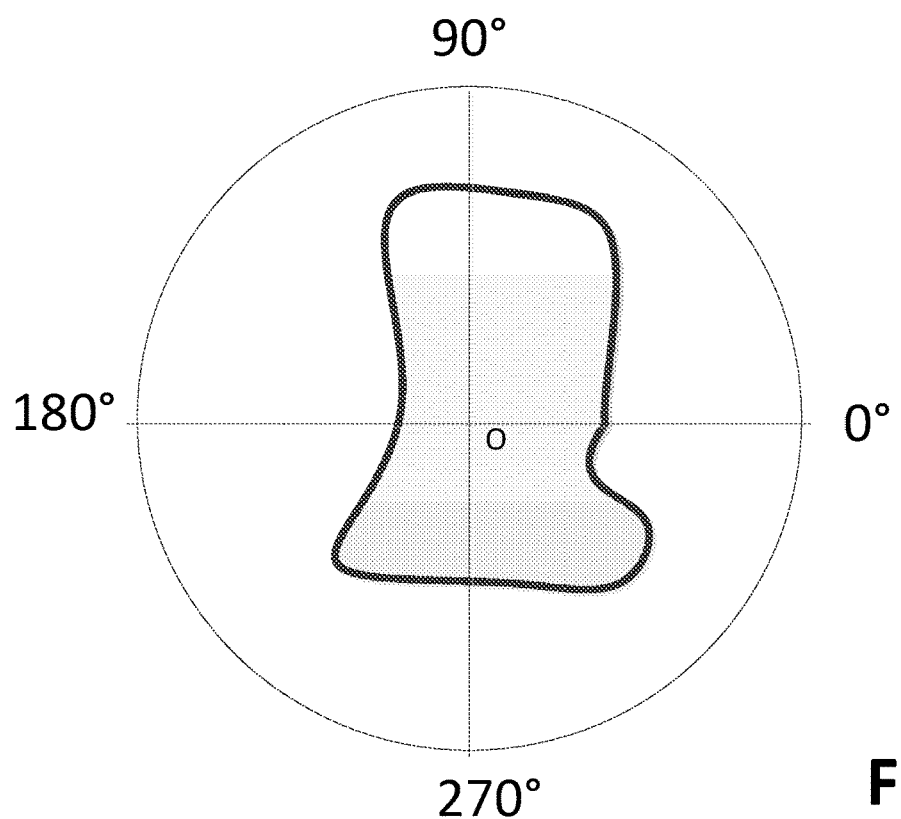

FIGS. 29B, and 29C and 29D illustrate axial and circumferential stiffness profiles, respectively, of prosthetic heart valve 800 (shown in FIG. 29A) according to an embodiment. The stiffness of heart valve 800 can vary axially and/or circumferentially in any suitable manner. For example, FIG. 29B represents an axial stiffness profile of valve 800. Specifically, as shown, the Z-axis represents an axial location on valve 800 (e.g., a location of the stiffness value). The S-axis represents a range of stiffness (or range of stiffness values), increasing from left (starting at origin O) to right.

Further to this example, as illustrated in FIG. 29B, in some embodiments, locations near the ventricle portion 822 (e.g., indicated as B in FIG. 29A) of the outer frame 822 can have a larger stiffness value, locations near the annulus portion 824 of the outer frame 820 can have a smaller stiffness value relative to the ventricle portion 822 (e.g., to facilitate cooperation with the native valve annulus), and locations near the atrium portion 826 (e.g., indicated as A in FIG. 29A) of the outer frame 820 can have a smaller, the same, or larger stiffness value (illustrated by the dotted line) than the stiffness value near the annulus portion 824. In this manner, the outer frame assembly 810 can be relatively more compliant in hoop compression in a central, annulus portion 814, than at the ventricle portion 812. Thus, in use, the prosthetic valve 800 can seat securely in the annulus of the native heart valve while imposing minimal loads on the inner valve assembly 840 that could degrade the performance of the valve leaflets 870. Although, for ease of illustration, the stiffness profile shown in FIG. 29B includes linear portions, in some embodiments, the stiffness profile can include non-linear portions instead of or in addition to the linear portions as shown.

Similarly, the stiffness of heart valve 800, or portions of heart valve 800, can have varying degrees of stiffness circumferentially, as illustrated by the stiffness profiles shown in FIGS. 29C and 29D. By way of example, FIG. 29C illustrates a circumferential stiffness profile at axial location A (as shown by reference 'A' in FIG. 29A). Similarly, FIG. 29D illustrates a circumferential stiffness profile at axial location B (as shown by reference 'B' in FIG. 29A). As the profile extends radially from the origin (indicated as 'O'), the stiffness value increases.

Thus, as shown in FIG. 29C, the stiffness at S1 (90 degrees) is greater than the stiffness at S2 (270 degrees). Further to this example, in some embodiments, the circumferential portion from zero to 180 degrees can represent a relatively flat portion of an outer frame 820 of the outer frame assembly 810 having a D-shape configuration, and 180 to 360 degrees can represent a relatively curved portion of the outer frame 820 having the D-shape configuration.

In a similar fashion, FIG. 29D illustrates a circumferential stiffness profile at axial location B (as shown by reference 'B' in FIG. 29A). As shown, axial location B has a different stiffness profile than axial location A. Such variability in design, as discussed above, can provide for advantageous customization of heart valve 800, and cooperation of heart valve 800 with a native heart valve. Similar to FIGS. 29C, 29D illustrates the stiffness at one side of valve 800 being be greater than a stiffness at another side of the valve 800. In this manner, in some instances, a portion of valve 800 that will experience greater forces from the native heart valve annulus can have a smaller stiffness value (e.g., more compliant) than a portion of the valve 800 that will experience smaller or fewer forces, thus optimizing the cooperation of the prosthetic heart valve 800 with the native heart (particularly the native heart valve annular region).

While various embodiments have been described above, it should be understood that they have been presented by way of example only, and not limitation, and as such, various changes in form and/or detail may be made. Any portion of the apparatus and/or methods described herein may be combined in any suitable combination, unless explicitly expressed otherwise. Where methods and/or schematics described above indicate certain events occurring in certain order, the ordering of certain events and/or flow patterns may be modified. Additionally, certain events may be performed concurrently in parallel processes when possible, as well as performed sequentially.

What is claimed is:
1. A prosthetic heart valve comprising:
an outer frame assembly having an atrium portion, a ventricle portion, and an annulus portion between the atrium portion and the ventricle portion,
the outer frame assembly having an hourglass shape and including shape memory material such that the outer frame assembly reverts to a memory shape in the absence of applied forces; and
an inner valve assembly including an inner frame having an atrium end and a ventricle end, the inner valve assembly coupled to the outer frame assembly by a connection between the ventricle end of the inner frame and the ventricle portion of the outer frame assembly, the inner frame assembly extending from the connection towards the atrium portion of the outer frame assembly, the inner frame assembly and the outer frame assembly diverging from each other in a direction from the connection towards the atrium portion of the outer frame assembly, the annulus portion of the outer frame assembly being spaced radially from the inner valve assembly and radially inwardly deflectable towards the inner valve assembly to accommodate in the annulus portion a natural valve annulus having a perimeter smaller than a minimum perimeter of the annulus portion when the outer frame assembly has the memory shape.

2. The prosthetic heart valve of claim 1, wherein each of the atrium portion and the annulus portion of the outer frame assembly is D-shaped in cross section.

3. The prosthetic heart valve of claim 1, wherein the inner valve assembly includes:
a covering disposed about a periphery of the inner frame and formed of a material substantially impermeable to blood; and
a valve leaflet assembly supported on the inner frame.

4. The prosthetic heart valve of claim 1, wherein the outer frame assembly includes:
an outer frame; and
an inner covering disposed about an inner periphery of the outer frame and formed of a material substantially impermeable to blood.

5. The prosthetic heart valve of claim 1, wherein:
the inner valve assembly includes a covering disposed about a periphery of the inner frame and formed of a material substantially impermeable to blood, and
the outer frame assembly includes an outer frame and an inner covering disposed about an inner periphery of the outer frame and formed of a material substantially impermeable to blood, the covering of the inner frame coupled to the inner covering of the outer frame.

6. The prosthetic heart valve of claim 1, further comprising:
a valve leaflet assembly supported on the inner frame.

7. The prosthetic heart valve of claim 1, wherein the annulus portion of the outer frame assembly has a perimeter that is sized to fit into an annulus of an atrioventricular valve, each of the atrium portion and the annulus portion of the outer frame assembly being D-shaped in cross section.

8. The prosthetic heart valve of claim 1, wherein:
the ventricle portion of the outer frame assembly has a maximum perimeter larger than a maximum perimeter of the annulus portion when the outer frame assembly has the memory shape, and
the ventricle portion of the outer frame assembly has a minimum perimeter smaller than the minimum perimeter of the annulus portion when the outer frame assembly has the memory shape.

9. A prosthetic heart valve comprising:
an outer frame assembly having an atrium portion, a ventricle portion, and an annulus portion between the atrium portion and the ventricle portion, the outer frame assembly including shape memory material such that the outer frame assembly reverts to a memory shape in the absence of applied forces,
the annulus portion having an hourglass shape with a minimum perimeter disposed between a larger perimeter near the atrium portion and a larger perimeter near the ventricle portion when the outer frame assembly has the memory shape; and
an inner valve assembly including an inner frame having an atrium end and a ventricle end,
the inner valve assembly coupled to the outer frame assembly by a connection between the ventricle end of the inner frame and the ventricle portion of the outer frame assembly,
the inner frame assembly extending from the connection towards the atrium portion of the outer frame assembly,
the inner frame assembly and the outer frame assembly diverging from each other in a direction from the connection towards the atrium portion of the outer frame assembly,
the annulus portion of the outer frame assembly being spaced radially from the inner valve assembly and radially inwardly deflectable towards the inner valve assembly to accommodate in the annulus portion a natural valve annulus having a perimeter smaller than the minimum perimeter of the annulus portion when the outer frame assembly has the memory shape,
the outer frame assembly having a stiffness in resistance to radial compression that varies in an axial direction of the outer frame assembly.

10. The prosthetic heart valve of claim 9, wherein each of the atrium portion and the annulus portion of the outer frame assembly is D-shaped in cross section.

11. The prosthetic heart valve of claim 9, further comprising:
a valve leaflet assembly supported on the inner frame.

12. The prosthetic heart valve of claim 9, wherein:
the inner valve assembly includes a covering disposed about a periphery of the inner frame and formed of a material substantially impermeable to blood, and
the outer frame assembly includes an outer frame and an inner covering disposed about an inner periphery of the outer frame and formed of a material substantially impermeable to blood, the covering of the inner frame coupled to the inner covering of the outer frame.

13. The prosthetic heart valve of claim 9, wherein:
the ventricle portion of the outer frame assembly has a maximum perimeter larger than a maximum perimeter of the annulus portion when the outer frame assembly has the memory shape, and
the ventricle portion of the outer frame assembly has a minimum perimeter smaller than the minimum perimeter of the annulus portion when the outer frame assembly has the memory shape.

* * * * *